(12) United States Patent
Borden et al.

(10) Patent No.: US 6,217,891 B1
(45) Date of Patent: *Apr. 17, 2001

(54) NON-HOST VOLATILES AS REPELLENTS FOR CONIFER-INFESTING BARK BEETLES

(75) Inventors: John H. Borden, Burnaby; Leslie J. Chong, Vancouver; Gerhard Gries; Regine Gries, both of Coquitlam; Dezene P. W. Huber; Harold D. Pierce, Jr., both of Burnaby; Ian M. Wilson, Vernon, all of (CA)

(73) Assignee: Simon Fraser University, Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/311,710

(22) Filed: May 13, 1999

Related U.S. Application Data

(63) Continuation-in-part of application No. 08/986,823, filed on Dec. 8, 1997.
(60) Provisional application No. 60/032,628, filed on Dec. 9, 1996.

(51) Int. Cl.$^7$ .......................... A01N 25/00; A01N 35/00; A01N 31/00; A01N 31/08

(52) U.S. Cl. .......................... 424/405; 514/675; 514/693; 514/699; 514/690; 514/724; 514/730

(58) Field of Search ................................... 514/693, 699, 514/675, 690, 724, 730; 424/405

(56) References Cited

U.S. PATENT DOCUMENTS

| | | | |
|---|---|---|---|
| 4,219,570 | 8/1980 | Inazuka et al. | 424/343 |
| 5,273,996 | * 12/1993 | Dickens et al. | 514/450 |
| 5,281,418 | 1/1994 | Lindgren et al. | 424/405 |
| 5,403,863 | 4/1995 | Hayes et al. | 514/717 |
| 5,468,770 | 11/1995 | Dickens et al. | 514/450 |
| 5,518,757 | 5/1996 | Hayes et al. | 427/4 |
| 5,721,274 | * 2/1998 | Vander Meer et al. | 514/532 |

FOREIGN PATENT DOCUMENTS

| | | |
|---|---|---|
| 04338309 | 11/1992 | (JP) . |
| 07242505 | 8/1995 | (JP) . |

OTHER PUBLICATIONS

Amman, G.D., et al. 1989. Efficacy of verbenone in reducing lodgepole pine infestation by mountain pine beetles in Idaho. *Can. J. For. Res.* 19: 60–64.*

Amman, G.D., et al. 1991. Optimum dosage of verbenone to reduce infestation of mountain pine beetle in lodgepole pine stands of central Idaho. USDA For. Serv. Res. Pap. INT–446.*

Bentz, B., et al. 1989. Does verbenone reduce mountain pine beetle attacks in susceptible stands of ponderosa pine? USDA For. Serv. Res. Note RM–495.*

Bertram, S.L., et al. 1994a. Response of *Dendroctonus brevicomis* LeConte (Coleoptera: Scolytidae) to different release rates and ratios of aggregation semiochemicals and the inhibitors verbenone and ipsdienol. *J. Chem. Ecol.* 20: 1617–1629.*

Bertram, S.L., et al. 1994b. Influence of aggregation inhibitors (verbenone and ipsdienol) on landing and attack behavior of *Dendroctonus brevicomis* (Coleoptera: Scolytidae) to different release rates and ratios of aggregation semiochemicals and the inhibitors verbenone and ipsdienol. *J. Chem. Ecol.* 20: 2931–2941.*

Birgersson, G., et al. 1995. Pheromones in white pine cone beetle, *Conophthorus coniperda* (Schwarz) (Coleoptera: Scolytidae). *J. Chem. Ecol.* 21: 143–167.*

Borden, J.H. 1985. Aggregation pheromones. pp. 257–285. In G.A. Kerkut and L.I. Gilbert (eds.) Comprehensive insect physiology, biochemistry and pharmacology, vol. 9. Pergammon Press, Oxford.*

Borden, J.H. 1996. Disruption of semiochemical–mediated aggregation in bark beetles. pp. 421–438. In R.T. Carde and A.K. Minks (eds.). Insect pheromone research: new directions. Chapman and Hall, New York.*

Borden, J.H., et al. 1988. The role of semiochemicals in IPM of the mountain pine beetle. pp. 247–255. In T.L. Payne and H. Saarenmaa. Integrated control of scolytid bark beetles. Virginia Polytechnic Institute and State Univ., Blacksburg, VA.*

Borden, J.H., et al. 1987. Response of the mountain pine beetle, *Dendroctonus ponderosae* Hopkins (Coleoptera: Scolytidae), to five semiochemicals in British Columbia lodgepole pine forests. *Can. J. For. Res.* 17: 118–128.*

Borden, J.H., et al. 1988. Assessment of two pine oil treatments to protect stands of lodgepole pine from attack by the mountain pine beetle. *J. Entomol. Soc. B.C.* 85:28–33.*

Borden, J.H., et al. 1992. Synomones of two sympatric species deter attack by the pine engraver, *Ips pini* (Coleoptera: Scolytidae) *Can. J. For. Res.* 22: 381–387.*

Borden, J.H., et al. 1993. A simplified tree bait for the mountain pine beetle. *Can. J. For. Res.* 23: 1108–1113.*

Byers, J.A. 1989. Chemical ecology of bark beetles. *Experienta* 45: 271–283.*

(List continued on next page.)

Primary Examiner—Jose' G. Dees
Assistant Examiner—Alton Pryor
(74) Attorney, Agent, or Firm—Oyen Wiggs Green & Mutala

(57) ABSTRACT

This invention relates to the use of volatiles from the bark of non-host angiosperm trees to protect coniferous trees from attack by bark beetles. Individual compounds or mixtures selected from 18 non-host bark volatiles, identified by coupled gas chromatographic-electroantennographic detection analysis, and deployed alone or with an antiaggregation pheromone or a green leaf volatile, or mixture thereof, are demonstrated to repel conifer-infesting bark beetles from attractant-baited traps, and to protect attractant-baited trees from attack.

24 Claims, 7 Drawing Sheets

OTHER PUBLICATIONS

Devlin, D.R., et al. 1994. Efficacy of antiaggregants for the pine engraver, *Ips pini* (Say) (Coleoptera: Scolytidae). *Can. J. For. Res.* 24: 2469–2476.*

Dickens, J.C., et al. 1992. Green leaf volatiles interrupt aggregation pheromone response in bark beetles infesting southern pines. *Experienta* 48: 523–524.*

Furniss, M.M., et al. 1982. Aerial applications of Douglas–fir beetle antiaggregation pheromone: equipment and evaluation. USDA For. Serv. Gen. Tech. Rep. INT–137.*

Gibson, K.E., et al. 1991. Mountain pine beetle response to different verbenone dosages in pine stands of western Montana. USDA For. Serv. Res. Pap. INT–444.*

Gries, G. 1995. Prospects of new semiochemicals and technologies. pp. 44–47. In S.M. Salom and K.R. Hobson (eds.) Application of semiochemicals for management of bark beetle infestations—proceedings of an informal conference. USDA For. Serv. Gen. Tech. Rep. INT–GTR–318.*

Hayes, J.L., et al. 1994. 4–Allylanisole as an inhibitor of bark beetle (Coleoptera: Scolytidae) aggregation. *J. Econ. Entomol.* 87: 1586–1594.*

Hayes, J.L., et al. 1994. Repellent properties of the compound 4–allylanisole to the southern pine beetle. *J. Chem. Ecol.* 20: 1595–1615.*

Hayes, J.L., et al. 1996. Suppression of bark beetles and protection of pines in the urban environment: a case study. *J. Arboriculture* 22: 67–74.*

Hobson, K.R. 1995. Host compounds as semiochemicals for bark beetles. pp. 48–51. In S.M. Salom and K.R. Hobson (eds.). Application of semiochemicals for management of bark beetle infestations—proceedings of an informal conference. USDA For. Serv. Gen. Tech. INT–GTR–318.*

Kline, L.N., et al. 1974. Repression of spruce beetle (Coleoptera) attraction by methylcyclohexenone in Idaho. *Can. Entomol.* 106: 485–491.*

Kostyk, B.C., et al. 1993. Photoisomerism of antiaggregation pheromone verbenone: biological and practical implications with respect to the mountain pine beetle, *Dendroctonus ponderosae* Hopkins (Coleoptera: Scolytidae). *J. Chem. Ecol.* 19: 1749–1959.*

Lindgren, B.S., et al. 1989a. Suppression of spruce beetle attacks by MCH released from bubble caps. *West. J. Appl. For.* 4: 49–52.*

Lindgren, B.S., et al. 19889b. Reduction of mountain pine beetle (Coleoptera: Scolytidae) attacks by verbenone in lodgepole pine stands in British Columbia. *Can. J. For. Res.* 19: 65–68.*

Lister, C.K., et al. 1990. Verbenone bubble caps ineffective as a preventive strategy against mountain pine beetle attacks in ponderosa pine. USDA For. Serv. Res. Note RM–501.*

McGregor, M.D., et al. 1984. MCH pheromone for preventing Douglas–fir beetle infestation in windthrown trees. *J. For.* 82: 613–616.*

McMullen, L.H., et al. 1985. Some effects of pine oil on mountain pine beetle (Coleoptera: Scolytidae) at different population levels. *J. Entomol. Soc. B.C.* 82: 29–30.*

Nijholt, W.W., et al. 1981. Pine oil protects living trees from attack by three bark beetle species, *Dendroctonus* spp. (Coleoptera: Scolytidae). *Can. Entomol.* 113: 337–340.*

O'Donnell, B.P., et al. 1986. Effect of pine oil on landing and attack by the southern pine beetle (Coleoptera: :Scolytidae). *J. Entomol. Sci.* 21: 319–321.*

Paine, T.D., et al. 1991. Response of *Dendroctonus brevicomis* and *Ips paraconfusus* (Coleoptera: Scolytidae) to combinations of synthetic pheromone attractants and inhibitors verbenone and ipsdienol. *J. Chem. Ecol.* 17: 2163–2176.*

Payne, T.L., et al. 1989. Evaluation of (S)–verbenone applications for suppressing southern pine beetle (Coleoptera: Scolytidae) infestations. *J. Econ. Entomol.* 82: 1702–1708.*

Payne, T.L., et al. 1992. Disruption of *Dendroctonus frontalis* (Coleoptera: Scolytidae) infestations with an inhibitor pheromone. *J. Appl. Entomol.* 114: 341–347.*

Pierce, H.D., Jr., et al. 1995. Pheromones in red pine cone beetle, *Conophthorus resinosae* Hopkins, and its synonym, *C. banksianae* McPherson (Coleoptera: Scolytidae). *J. Chem. Ecol.* 21: 169–185.*

Richmond, C.E. 1985. Effectiveness of two pine oils for protecting lodgepole pine from attack by the mountain pin beetle (Coleoptera: Scolytidae). *Can. Entomol.* 117: 1445–1446.*

Rudinsky, J.A. 1973. Multiple functions of the Douglas–fir Beetle pheromone 3–methyl–2–cyclohexen–1–one. *Environ. Entomol.* 2: 579–585.*

Rudinsky, J.A., et al. 1974. Granular formulation of methylcyclohexenone: an antiaggregative pheromone of the Douglas–fir beetle and spruce bark beetles. *Z. angew. Entomol.* 75: 254–263.*

Ryker, L.C., et al. 1983. Effect of verbenone on aggregation of *Dendroctonus ponderosae* Hopkins (Coleoptera: Scolytidae) to synthetic attractant. *Z. angew. Entomol.* 96: 452–459.*

Shea, P.J., et al. 1992. Aerial application of verbenone reduces attack of lodgepole pine by the mountain pine beetle. *Can. J. For. Res.* 22: 436–441.*

Strom, B.L., et al. 1995. Naturally occurring compound can protect southern pines from the southern pine beetle. Louisiana Agriculture 38(4): 5–7.*

Strom, B.L., et al. 1996. Variation in concentration of 4–allylanisole in oleoresin of southern pines. USDA For. Serv., S. For. Exp. Sta., SPB Update, Oct. 1996: 2.*

Visser, J.H. 1986. Host odor perception in phytophagous insects. *Annu. Rev. Entomol.* 31: 121–144.*

Werner, R.A. 1995. Toxicity and repellency of 4–allylanisole and monoterpenes from white spruce and tamarak to the spruce beetle and eastern larch beetle (Coleoptera: Scolytidae). *Environ. Entomol.* 24: 372–379.*

Werner, R.A., et al. 1986. Evaluation of pine oil for protecting white spruce from spruce beetle (Coleoptera: Scolytidae) attack. *J. Entomol. Soc. B.C.* 83: 3–5.*

Wilson, I.M., et al. 1996. Green leaf volatiles as antiaggregants for the mountain pine beetle, *Dendroctonus ponderosae* Hopkins (Coleoptera: Scolytidae). *J. Chem. Ecol.* 22: 1861–1875.*

* cited by examiner

NON-HOST VOLATILES AS REPELLENTS FOR CONIFER-INFESTING BARK BEETLES

This application is a continuation-in-part of application Ser. No. 08/986,823, filed Dec. 8, 1997. This application claims the priority date of provisional 60/032,628 filed Dec. 9, 1996.

FIELD OF THE INVENTION

This invention relates to a method and compositions for preventing or limiting the attack and infestation of coniferous trees (Class Gymnospermae) by conifer-infesting bark beetles by using volatile substances from non-host hardwood trees (Class Angiospermae), alone or in combination with other suitable substances, as behavioral modifiers that disrupt the response of these beetles to attractive host volatiles and beetle-produced pheromones.

BACKGROUND OF THE INVENTION

Bark beetles are insects in the family Scolytidae (Order Coleoptera) that mine in the bark of the bole of many species of trees; certain species are capable of killing their hosts, by mechanically girdling the tree, by inoculating a lethal fungus in to the tree, or both. Bark beetles in this instance are considered to be separate from beetles in the same family that mine in other parts of coniferous trees, e.g. cones, twigs and wood.

Repellents in this instance are defined as agents that impede or prevent successful attack by bark beetles on host logs, stumps, trees or stands through interference with the natural responses by these insects to attractive host volatiles and beetle-produced pheromones. Synonyms include: disruptants, deterrents, interruptants, and inhibitors.

Chemical signals are very important in regulating the behavior of conifer-infesting bark beetles. Attraction to and mass-attack of uninfested host trees is mediated by blends of volatile compounds from the bark of trees in combination with aggregation pheromones produced by either or both sexes of attracting beetles (Borden 1985; Byers 1989). For example, attack by the mountain pine beetle, *Dendroctonus ponderosae*, is mediated by a blend of host tree monoterpenes, principally myrcene, in combination with the aggregation pheromones, trans-verbenol and exo-brevicomin, produced by attacking females and males, respectively (Borden et al. 1987). Both sexes respond to this attractive composition. As the bark becomes fully occupied, the attacking beetles produce the antiaggregation pheromone, verbenone, which disrupts response to the above attractants (Ryker and Yandell 1983). In so doing, it deters further attack on a tree (Borden and Lindgren 1988), and causes incoming beetles to shift their attack toward neighbouring trees.

Numerous attempts have been made to find inexpensive volatile compounds or compositions that can effectively disrupt the host selection and mass-attack behavior of conifer-infesting bark beetles (Borden 1996). These substances could then be used to protect individual trees or stands from attack. The substances tested include antiaggregation pheromones, pheromones of competing species, green leaf volatiles and host tree constituents.

Two antiaggregation pheromones have shown the potential for practical disruptant activity against conifer-infesting bark beetles. 3,2-MCH (3-methylcyclohex-2-en-1-one) produced by the Douglas-fir beetle, *Dendroctonus pseudotsugae,* caused a significant reduction of the response of both sexes to attractant-baited traps (Rudinsky 1973). When dispensed aerially in a granular formulation, 3,2-MCH effectively protected vulnerable host logs from attack (Furniss et al. 1981, 1982; McGregor et al. 1984). 3,2-MCH is also produced by the spruce beetle, *Dendroctonus rufipennis*. In field experiments, 3,2-MCH strongly repelled spruce beetles from attractant-baited traps and from logs treated with vials, granules or bubble caps releasing 3,2-MCH (Kline et al. 1974; Rudinsky et al. 1974; Lindgren et al. 1989a). The antiaggregation pheromone, verbenone, effectively disrupted attack by the mountain pine beetle when deployed in stands of lodgepole pine in slow-release devices affixed to trees (Amman et al. 1989, 1991; Lindgren et al. 1989b, 1994), or broadcast in a granular formulation from the air (Shea et al. 1992). However, the efficacy of verbenone against the mountain pine beetle was inconsistent between years, geographic locations, and tree species (Bentz et al. 1989; Lister et al. 1990; Gibson et al. 1991; Shea et al. 1992). The inconsistency of verbenone is accentuated by its conversion to an insert substance, chrysanthanone, on exposure to ultraviolet light (Kostyk et al. 1993). Against the southern pine beetle, *Dendroctonus frontalis,* verbenone was effective in controlling spot infestations when trees at the advancing front were treated with verbenone, and freshly-attacked trees were felled, causing both olfactory and visual disruption (Payne and Billings 1989; Payne et al. 1992).

A third pheromone, conophthorin, (E)-7-methyl-1,6-dioxaspiro[4.5]decane, acts as a repellent for male cone beetles, Conophthorus species (Birgersson et al. 1995; Pierce et al. 1995), and as an antiaggregation pheromone for the ash bark beetle, *Leperisinus varius* (Kohnle 1985). It has not been found in any species of conifer-infesting bark beetle, nor has it been tested for bioactivity against any such beetle.

In some cases, pheromones of bark beetles that compete with the target species for the inner bark can act alone or enhance the repellency of an antiaggregation pheromone. For example, when ipsdienol, a pheromone common to Ips species was deployed with the antiaggregation pheromone, verbenone, the two compounds acted synergistically to disrupt response by the western pine beetle, *Dendroctonus brevicomis,* to attractant-baited traps and ponderosa pine trees (Paine and Hanlon 1991; Bertram and Paine 1994a,b). Similarly, verbenone produced by the mountain pine beetle and ipsenol produced by *Ips latidens* acted synergistically to disrupt attack on felled lodgepole pine trees by the pine engraver, *Ips pini* (Borden et al. 1992; Devlin and Borden 1994).

Another source of repellents lies in green leaf volatiles, six-carbon alcohols, aldehydes and derivative esters commonly found in green plants (Visser 1986). Two green leaf volatiles, 1-hexanol and hexanal, were shown to be moderately effective disruptants of the pheromone response of the southern pine beetle and two Ips species (Dickens et al. 1992, 1993, 1995). When a wider array of green leaf volatiles was tested against the mountain pine beetle, hexanal was found to be inactive, 1-hexanol was a moderately effective repellent, and two other compounds, (E)-2-hexen-1-ol and (Z)-3-hexen-1-ol, were very effective in repelling both sexes from attractant-baited traps and trees (Wilson et al. 1996).

Of the host tree compositions tested as attack disruptants for conifer-infesting bark beetles, one of them, pine oil, is a crude mixture of monoterpenes and many other unknown constituents. When sprayed to the drip point onto the lower bole of attractant baited trees pine oil disrupted attack for varying periods of time by the mountain pine beetle (Nijholt et al. 1981; McMullen and Safranyik 1985; Richmond 1985), the spruce beetle (Nijholt et al. 1981; Werner et al. 1986), the Douglas-fir beetle (Nijholt et al. 1981), and the southern pine beetle (O'Donnell et al. 1986). However, spraying the bole with pine oil was not effective in preventing attack by the black turpentine beetle, *Dendroctonus terebrans,* or by the eastern fivespined ips, *Ips grandicollis* (Berisford et al. 1986), nor was it recommended as an area-wide operational treatment for the mountain pine beetle (Borden et al. 1988).

The other host tree volatile with practical potential as a disruptant is 4-allylanisole (also known as estragole and methyl chavecol), a compound that comprises about 1.0% of the xylem oleoresin of loblolly pines (Strom et al. 1996). At generally very high doses, e.g. 160 mg per 24 h, 4-allylanisole and three of its analogs (Hayes et al. 1995 a, b) disrupted the responses to attractant-baited traps by the southern pine beetle (Hayes et al. 1994), the mountain pine beetle (Hayes and Strom 1994; Hobson 1995), the western pine beetle (Hobson 1995), and the pine engraver (Hayes and Strom 1994). A much lower dose of 0.1 mg per 24 h was effective for the spruce beetle and the eastern larch beetle, *Dendroctonus simplex* (Werner 1995). When deployed from open vials suspended from ropes hung vertically on the boles of southern pines, 4-allylanisole provided effective protection against the southern pine beetle (Strom et al. 1995; Hayes et al. 1996).

Schroeder (1992) showed that if bolts of aspen, *Populus tremula,* or birch, *Betula pendula,* were hung beside traps baited with ethanol, the European bark beetles, *Tomicus piniperda* and *Hylurgops palliatus,* were repelled. However, in no case has there been a scientific investigation of the means by which conifer-infesting bark beetles use specific volatile chemicals to detect and avoid non-host angiosperm tree species. In nature, attack of these trees would result in death of the attacking beetles. We reasoned that the beetles' life or death decision whether or not to attack a given tree is so important, that we would be likely to discover new repellents for bark beetles in the volatiles emitted by non-host angiosperm trees.

SUMMARY OF THE INVENTION

We have discovered unexpectedly a blend of volatiles from the bark of non-host angiosperm trees, the constituents of which are perceived by the antennae of conifer-infesting bark beetles, and which disrupt the response of these bark beetles to attractant-baited traps and trees. These volatiles may be employed in a composition, either alone or in various combinations with each other, or in combination with other known repellents, such as certain organic compounds and anti-aggregation pheromones, for the protection from attack of susceptible logs, trees and stands, and for the control of populations of conifer-infesting bark beetles.

In accordance with this discovery, it is an object of this invention to provide compositions for preventing or limiting the attack and infestation of conifer trees by conifer-infesting bark beetles by disrupting the response of these beetles to attractive host tree volatiles and the beetles' aggregation pheromones.

In general terms, the invention is directed to a method of repelling conifer-infesting bark beetles from a surface subject to attack by said beetles, comprising treating the surface with a repellent compound selected from the group consisting of: toluene, pentanol, 2-hexanone, 3-hexanone, heptanal, benzaldehyde, 2-hydroxycyclohexanone, benzyl alcohol, (E)-ocimene, salicylaldehyde, conophthorin, guiacol, nonanal, methylsalicylate, decanal, thymolmethylether, (E)-nerolidol and dendrolasin, or mixture thereof, in amounts sufficient to repel said beetles from said surface, or eluting said compound in amounts sufficient to repel said beetles from said surface from inert devices or carriers applied to said surface from which said beetles are to be repelled.

The invention is also directed to a method of protecting individual logs, trees and groups of coniferous tree hosts from attack by conifer-infesting bark beetles, comprising treating said logs, trees and groups of coniferous tree hosts with a repellent compound selected from the group consisting of: toluene, pentanol, 2-hexanone, 3-hexanone, heptanal, benzaldehyde, 2-hydroxycyclohexanone, benzyl alcohol, (E)-ocimene, salicylaldehyde, conophthorin, guiacol, nonanal, methylsalicylate, decanal, thymolmethylether, (E)-nerolidol and dendrolasin, or mixtures thereof.

The repellent compound or mixture can be combined with one or more green leaf volatiles selected from the group consisting of hexanal, (E)-2-hexenal, 1-hexanol, (E)-2-hexen-1-ol, (Z)-2-hexen-1-ol, and (Z)-3-hexen-1-ol, and mixtures thereof.

The repellent compound or mixture can also be combined with one or more antiaggregation pheromones selected from the group consisting of verbenone and 3-methylcyclohex-2-ene-1-one.

The repellent compound or mixture can be combined with both a green leaf volatile, or mixtures thereof, and an antiaggregation pheromone selected from the group consisting of verbenone and 3-methylcyclohex-2-ene-1-one.

The conifer-infesting bark beetles can be any one or more of the group consisting of *Dendroctonus ponderosae, Dendroctonus rufipennis, Dendroctonus pseudotsugae, Ips pini,* and *Dryocoetes confusus.*

The invention also pertains to a composition for repelling conifer-infesting bark beetles comprising an effective amount of a repellent compound selected from the group consisting of: toluene, pentanol, 2-hexanone, 3-hexanone, heptanal, benzaldehyde, 2-hydroxycyclohexanone, benzyl alcohol, (E)-ocimene, salicylaldehyde, conophthorin, guiacol, nonanal, methylsalicylate, decanal, thymolmethylether, (E)-nerolidol and dendrolasin, or mixtures thereof.

The repellent composition above can be combined with a green leaf volatile selected from the group consisting of hexanal, (E)-2-hexenal, 1-hexanol, (E)-2-hexen-1-ol, (Z)-2-hexen-1-ol, and (Z)-3-hexen-1-ol, and mixtures thereof. The repellent composition above can be combined with an antiaggregation pheromone selected from the group consisting of verbenone and 3-methylcyclohex-2-ene-1-one.

The repellent composition above can be combined with both a green leaf volatile, or mixtures thereof, and an antiaggregation pheromone selected from the group consisting of verbenone and 3-methylcyclohex-2-ene-1-one.

BRIEF DESCRIPTION OF THE DRAWINGS

In drawings which illustrate specific embodiments of the invention, but which should not be construed as restricting the spirit or scope of the invention in any way.

DETAILED DESCRIPTION OF THE INVENTION

Figure 1:
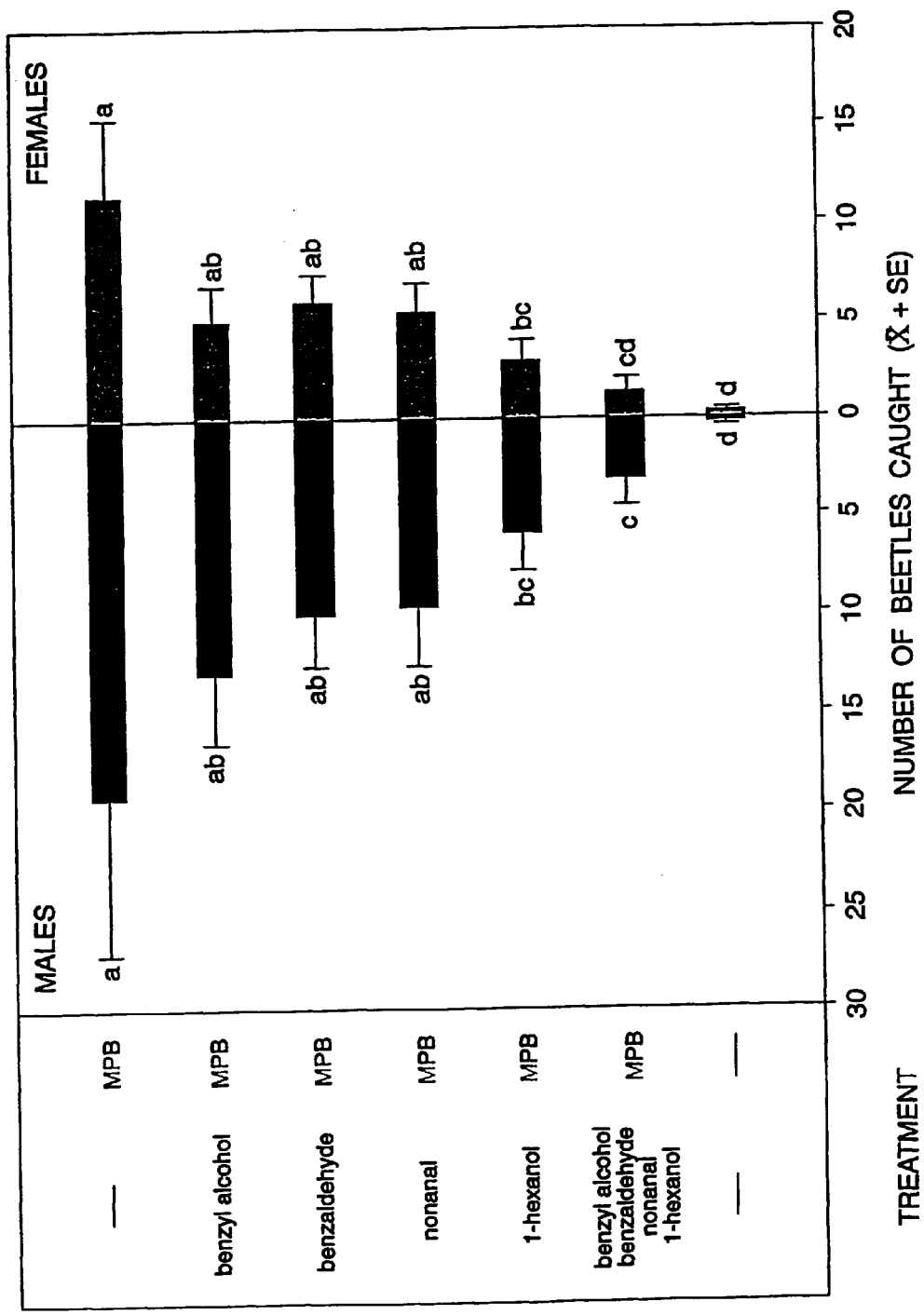
FIG. 1 illustrates a plot of the results of a first experiment showing the numbers of male and female mountain pine beetles captured in multiple-funnel traps baited with the attractant blend of exo-brevicomin, trans-verbenol and myrcene alone or in combination with three non-host volatiles and the green leaf volatile, 1-hexanol, alone or in quaternary combination. Willis Creek, near Princeton, B.C., July 20–26 and Aug. 16–31, 1995, n=17. Data transformed by $\log_{10}$ (x+1) and analyzed by ANOVA and the REGW test. Bars within a sex associated with the same letter are not significantly different, P<0.05. Horizontal lines in the treatment columns indicate no treatment.

This invention constitutes a novel approach to preventing or limiting attack on coniferous trees and woods by conifer-infesting bark beetles in that it exploits the repellent properties of the bark volatiles of non-host trees that the beetles avoid in nature.

The cost, the requirement for large dosages, and the lack of complete efficacy variably associated with known repellents for conifer-infesting bark beetles has limited their practical application. We have discovered compounds taken from the bark of non-host angiosperm trees that alone, or in various combinations, disrupt the response of conifer-infesting bark beetles to attractant-baited traps or host trees. According to this invention, there is provided a composition for controlling bark beetles that includes any number of compounds selected from the following chemicals: toluene, pentanol, 2-hexanone, 3-hexanone, heptanal, benzaldehyde, 2-hydroxycyclohexanone, benzyl alcohol, (E)-ocimene, salicylaldehyde, conophthorin, guaiacol, nonanal, methylsalicylate, decanal, thymolmethylether, (E)-nerolidol and dendrolasin.

The selected compounds may be employed with one or more additional known repellents of conifer-infesting bark beetles. Such suitable additional repellents include, but are not limited to, antiaggregation pheromones, including verbenone and 3,2-MCH, pheromones of bark beetles that may in nature compete with the target species, host volatiles, including 4-allylanisole, and green leaf volatiles, including hexanal, (E)-2-hexenal, 1-hexanol, (E)-2-hexen-1-ol, (Z)-2-hexen-1-ol, and (Z)-3-hexen-1-ol.

The volatiles of the inventive composition are applied according to the art in slow-release devices, materials and formulations that include, but are not limited to: bubble caps and other devices comprising a reservoir with a permeable barrier through which volatiles are slowly released; volatile-impregnated synthetic polymers in various shapes, such as pellets, granules and ropes; volatile-impregnated inert natural solids such as clays, cellulose and rubber; and volatile-containing liquid formulants, such as natural oils, organic solvents and water. Effective concentrations of the non-host volatiles in the composition may vary between about 0.1% and 99.9%. Concentrations and amounts of the volatile constituents, as well as the selection and amounts of additional repellents, may be determined by practitioners skilled in the art. Use of inexpensive non-host volatiles may lower the amount of other more expensive repellents required to protect host logs or trees from attack. In use, the repellent composition will be applied directly on, beside or in the vicinity of the trees or logs to be protected from attack.

The following examples demonstrate the natural occurrence, bioactivity and effectiveness of the non-host volatile composition as a repellent for conifer-infesting bark beetles. The examples describing field experiments primarily on the mountain pine beetle are intended to further illustrate the invention, and are not intended to limit the scope of the invention which is defined by the claims. Moreover, in order to demonstrate repellent activity, the examples all challenged the new non-host volatile compositions to inhibit the response of beetles to traps and trees baited with powerful attractants. In operational use, synthetic attractants would not be present, and the repellent effect would be even greater than shown in the examples.

EXAMPLE 1

We felled living trees of the following species: bigleaf maples, *Acer macrophyllum;* red alder, *Alnus rubra;* Sitka alder, *Alnus viridis;* paper birch, *Betula papynifera;* trembling aspen, *Populus tremuloides;* and western balsam poplar, *Populus trichocarpa.* Bolts were cut from the logs, transported to the laboratory and the bark stripped off. The bark was cut into small pieces, and for each species approximately 1 kg of the cut bark was placed in an aeration chamber for 5 days. Volatiles from aerations were captured on Porapak-Q and recovered by extraction with pentane.

Bolts were cut from trees infested with mountain pine beetles, spruce beetles, Douglas-fir beetles, pine engravers or the western balsam bark beetle, *Dryocoetes confusus,* and placed in cages in the laboratory. Emerged beetles were removed from cages daily and used immediately in coupled gas chromatographic-electroantennographic detection (GC-EAD) analysis modified for testing scolytids (Gries 1995) and employing a Varian 3400 gas chromatograph equipped with a fused silica column (DB-5, 30 m×0.32 mm). Electrodes were placed into the head (indifferent electrode) and antennal club (recording electrode) of living beetles (both sexes) of each of the above species. Antennally-active compounds in angiosperm bark volatile extracts were identified using coupled GC-mass spectrometry (MS) (Hewlett Packard 5985B) in full-scan electron impact and chemical ionization (isobutane) mode and by co-elution with authentic samples.

Antennally-active compounds, with their source species, and species of bark beetle with antennae sensitive to those compounds, are given in Table 1. Four of these compounds, 1-hexanol, hexanal, (E)-2-hexenal, and (Z)-3-hexen-1-ol, are green leaf volatiles. The first two were previously shown to be repellent to southern pine beetles (Dickens et al. 1992, 1993, 1995); hexanol, and (Z)-3-hexen-1-ol were repellent to mountain pine beetles (Wilson et al. 1996). Four others, 3-carene, limonene, α-pinene, and β-pinene are monoterpenes known to be present in the oleoresin of coniferous trees; all are known to be involved in some measure in blends of compounds that are attractive to one or more conifer-infesting bark beetles (Borden 1985). 4-Allylanisole is also a known repellent for four species of conifer-infesting bark beetles (Hayes and Strom 1994; Hayes et al. 1994, 1995a, b; Hobson 1995). All of the other compounds are shown for the first time to be perceived by the antennae of conifer-inhabiting bark beetles, and because these beetles avoid the bark of the source trees, to have potential repellent activity. Three of these compounds, benzyl alcohol, benzaldehyde and nonanal, elicited consistently strong antennal responses and were selected for detailed experimentation with the mountain pine beetle (Examples 2–6) to determine their repellent activity alone, and to determine how they interact with each other, with the green leaf volatile, 1-hexanol, and with the antiaggregation pheromone, verbenone.

TABLE I

Compounds from non-host angiosperm tree bark identified by coupled gas chromatographic-electoantennographic detection analysis as stimulating the antennal receptors of bark beetles infesting coniferous trees in the genera Pinus, Picea, Abies and Pseudotsuga. Identities confirmed by mass spectroscopy and comparison with authentic samples. Retention indices based on straight-chain hydrocarbons with same number of carbon atoms given for each compound, based on analyses with a DB-5 column with temperature programmed at 50° C. for 1 min, increasing at 10° C. per min to 240° C. Source species (with acronym used in table in parentheses) are: red alder (RA), *Alnus rubra;* Sitka alder (SA), *Alnus viridis;* bigleaf maple (BLM), *Acer macrophyllum;* paper birch (PB), *Betula papyrifera;* western balsam poplar (BP), *Populus trichocarpa;* and trembling aspen (TA), *Populus tremuloides.* Stimulated species are: mountain pine beetle (MPB), *Dendroctonus ponderosae;* Douglas-fir beetle (DFB), *Dendroctonus pseudotsugae;* spruce beetle (SB), *Dendroctonus rufipennis;* pine engraver (PE), *Ips pini;* and western balsam bark beetle (WBBB), *Dryocoetes confusus.*

| Retention index (K.I.) | Trivial name | IUPAC name, if different from trivial name | Source species | Stimulated species |
|---|---|---|---|---|
| 332 | pentanol | 1-pentanol | BP, TA, PB, SA | DFB |
| 335 | toluene | methylbenzene | BP, TA | DFB |
| 369 | 3-hexanone | | BP | DFB, MPB, SB, WBBB |
| 378 | 2-hexanone | | BP, SA | DFB |
| 800 | hexanal | | BP, TA, BLM, PB, RA, SA | DFB, MPB, SB, PE, WBBB |
| 853 | (E)-2-hexenal | | TA, PB | DFB, MPB, SB, PE, WBBB |
| 854 | (z)-3-hexen-1-ol | | BP | DFB, MPB, SB |
| 867 | hexanol | 1-hexanol | BP, TA, PB, SA | DFB, MPB, SB, WBBB |
| 901 | heptanal | | BP | DFB |
| 941 | α-pinene | 2-pinene | BP, BLM, PB, RA, SA | DFB, MPB, SB, WBBB |

TABLE I-continued

Compounds from non-host angiosperm tree bark identified by coupled gas chromatographic-electoantennographic detection analysis as stimulating the antennal receptors of bark beetles infesting coniferous trees in the genera Pinus, Picea, Abies and Pseudotsuga. Identities confirmed by mass spectroscopy and comparison with authentic samples. Retention indices based on straight-chain hydrocarbons with same number of carbon atoms given for each compound, based on analyses with a DB-5 column with temperature programmed at 50° C. for 1 min, increasing at 10° C. per min to 240° C. Source species (with acronym used in table in parentheses) are: red alder (RA), *Alnus rubra*; Sitka alder (SA), *Alnus viridis*; bigleaf maple (BLM), *Acer macrophyllum*; paper birch (PB), *Betula papyrifera*; western balsam poplar (BP), *Populus trichocarpa*; and trembling aspen (TA), *Populus tremuloides*. Stimulated species are: mountain pine beetle (MPB), *Dendroctonus ponderosae*; Douglas-fir beetle (DFB), *Dendroctonus pseudotsugae*; spruce beetle (SB), *Dendroctonus rufipennis*; pine engraver (PE), *Ips pini*; and western balsam bark beetle (WBBB), *Dryocoetes confusus*.

| Retention index (K.I.) | Trivial name | IUPAC name, if different from trivial name | Source species | Stimulated species |
|---|---|---|---|---|
| 949 | frontalin | 1,5-dimethyl-6,8-dioxabicylo [3.2.1] octane | RA, SA | DFB, MPB, SB |
| 969 | benzaldehyde | | BP, TA | DFB, MPB, SB, WBBB |
| 986 | β-pinene | 2(10)-pinene | BP, BLM, PB, RA, SA | DFB, MPB, SB, WBBB |
| 1002 | 2-hydroxycyclo-hexanone | | BP | SB |
| 1016 | 3-carene | | BP, BLM | DFB, MPB, SB |
| 1038 | limonene | 1,8-p-menthadiene | BLM, PB, RA | DFB, MPB, SB, PE |
| 1038 | β-phellandrene | 1(7), 2-p-menthadiene | BLM, PB, RA | DFB, MPB, SB, PE |
| 1042 | benzyl alcohol | | BP, TA | DFB, MPB, SB, PE |
| 1052 | (E)-ocimene | 3,7-dimethyl-1,3 (E), 6-octatriene | RA, SA | DFB, MPB, SB |
| 1056 | salicylaldehyde | 2-hydroxy-benzaldehyde | BP, TA | DFB, MPB, SB, PE, WBBB |
| 1062 | conophthorin | (E)-7-methyl-1,6-dioxaspiro[4.5]decane | BP, TA, BLM, PB | DFB, MPB, SB, PE, WBBB |
| 1093 | guiacol | 2-methoxyphenol | BP, TA, BLM, PB | DFB, MPB, SB, PE, WBBB |
| 1106 | nonanal | | BP, TA, BLM, PB, SA | DFB, MPB, SB, PE, WBBB |
| 1194 | methylsalicylate | methyl-2-hydroxybenzoate | RA | DFB |
| 1205 | 4-allylanisole | 1-methoxy-4-(2-propenyl) benzene | PB | DFB, SB |
| 1205 | decanal | | RA | DFB |
| 1234 | thyolmethylether | 1-isopropyl-2-methoxy-4-methylbenzene | BP | DFB |
| 1564 | (E)-nerolidol | (E)-3,7,11-trimethyl-1,6,10-dodecatrien-3-ol | BP | DFB |
| 1566 | dendrolasin | (E)-3-(4,8-dimethyl-3,7-nonadienyl)-furan | BP | DFB |

EXAMPLE 2

Experiment 1 was conducted from Jul. 20–26, 1995 (10 replicates) and Aug. 16–31, 1995 (7 replicates) in the valley of Willis Creek, 24 to 28 km south of Princeton, B.C. Twelve-unit multiple-funnel traps (Phero Tech Inc., Delta, B.C.) were set up 15 m apart along the margins of clearcut blocks adjacent to stands of mountain pine beetle-infested lodgepole pines. Treatments were deployed in traps as randomized complete blocks. Benzyl alcohol, benzaldehyde, nonanal and hexanol were tested alone and in quarternary combination for their ability to reduce attraction to lures (Phero Tech Inc.) releasing an attractive blend (Borden et al. 1987) of the pheromones trans-verbenol and exo-brevicomin plus the host kairomone, myrcene. Release devices (Phero Tech Inc.) were: 15 mL polyethylene bottle (myrcene), polyurethane flex lures (exo-brevicomin) and bubble caps (all other compounds). Respective release rates (mg per 24 h) determined in the laboratory at 22° C. (except for 1-hexanol at 24° C.) for exo-brevicomin, trans-verbenol, myrcene, benzaldehyde, benzyl alcohol, nonanal and 1-hexanol were: 0.05, 1.0, 18.0, 11.0, 3.5, 8.5, and 7.5.

Captured beetles were held at −4.0° C. until they could be sexed and counted. Trap catch data were transformed by $\log_{10} (x+1)$ to satisfy assumptions of normality and homogeneity of variance and then analyzed by ANOVA and the Ryan, Einot, Gabriel, Welsh (REGW) multiple range test ($\alpha=0.05$).

FIG. 1 illustrates a plot of the results of a first experiment showing the numbers of male and female mountain pine beetles captured in multiple-funnel traps baited with the attractant blend of exo-brevicomin, trans-verbenol and myrcene alone or in combination with three non-host volatiles and the green leaf volatile, 1-hexanol, alone or in quaternary combination. Willis Creek, near Princeton, B.C., July 20–26 and Aug. 16–31, 1995, n=17. Data transformed by $\log_{10}$ (x+1) and analyzed by ANOVA and the REGW test. Bars within a sex associated with the same letter are not significantly different, P<0.05. Horizontal lines in the treatment columns indicate no treatment.

Only 1-hexanol reduced the trap catches to levels significantly lower than to the attraction lures (FIG. 1), reductions of approximately 69% and 75% for males and females, respectively. However, the quarternary blend was more strongly repellent, approximately 83% and 89% for males and females, respectively, reducing trap catches for females to a level not significantly different from that in unbaited control traps. Thus addition of benzyl alcohol, benzaldehyde and nonanal to the green leaf volatile, 1-hexanol, increased the repellent effect over that caused by hexanol alone.

EXAMPLE 3

Experiment 2 followed the same experimental protocol at the same location as Experiment 1. It was conducted from Aug. 3–16, 1995 and had 10 replicates in which benzyl alcohol, benzaldehyde, nonanal and 1-hexanol were tested in all six possible binary combinations and in quarternary combination for their ability to disrupt response by the mountain pine beetle to multiple-funnel traps baited with trans-verbenol, exo-brevicomin and myrcene.

Figure 2:
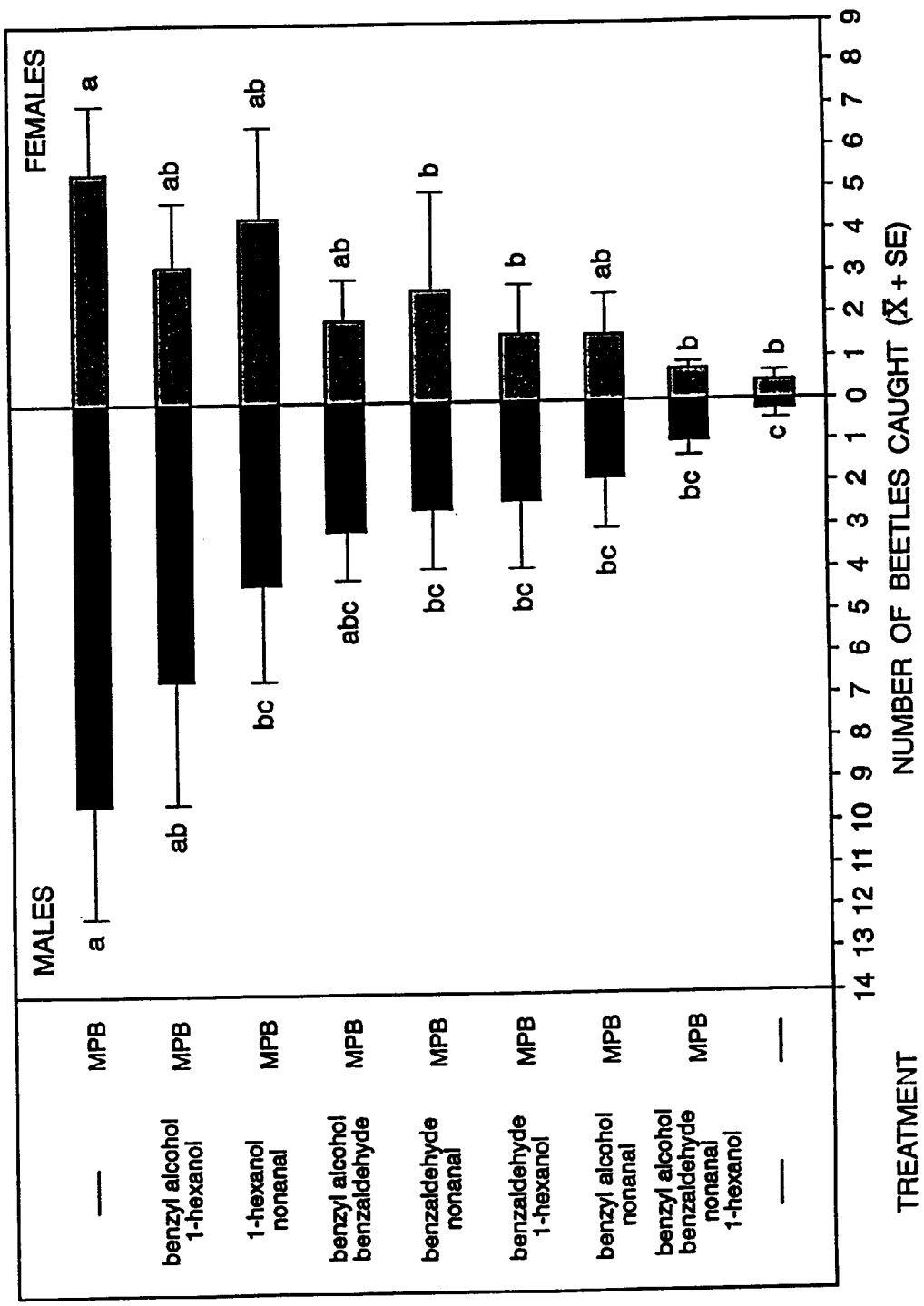
FIG. 2 illustrates a plot of the results of a second experiment showing the numbers of male and female mountain pine beetles captured in multiple-funnel traps baited with the attractant blend of exo-brevicomin, trans-verbenol and myrcene alone or in combination with three non-host volatiles and the green leaf volatile, 1-hexanol, in all possible binary combinations and in quaternary combination. Willis Creek, near Princeton, B.C., Aug. 3–16, 1995, n=10. Data transformed by $\log_{10}$ (x+1) and analyzed by ANOVA and the REGW test. Bars within a sex associated with the same letter are not significantly different, P<0.05. Horizontal lines in the treatment columns indicate no treatment.

FIG. 2 illustrates a plot of the results of a second experiment showing the numbers of male and female mountain pine beetles captured in multiple-funnel traps baited with the attractant blend of exo-brevicomin, trans-verbenol and myrcene alone or in combination with three non-host volatiles and the green leaf volatile, 1-hexanol, in all possible binary combinations and in quaternary combination. Willis Creek, near Princeton, B.C., Aug. 3–16, 1995, n=10. Data transformed by $\log_{10}$ (x+1) and analyzed by ANOVA and the REGW test. Bars within a sex associated with the same letter are not significantly different, P<0.05. Horizontal lines in the treatment columns indicate no treatment.

As shown in FIG. 2, four and two of the six binary blends significantly reduced catches of male and female mountain pine beetles, respectively. All three non-host volatiles were included in at least one bioactive binary blend against males, whereas benzyl alcohol was excluded from the active blends for females. As in Experiment 1, the lowest numerical catches were in traps releasing the quarternary blend. The blend of benzaldehyde plus nonanal caused significant disruption of the response by both sexes to attractant baited traps, and the blend of benzyl alcohol plus nonanal caused a significant reduction in the response of males. Therefore, benzyl alcohol, benzaldehyde and nonanal are shown to be new repellents for conifer-infesting bark beetles.

The four binary blends of 1-hexanol plus nonanal, benzaldehyde plus nonanal, benzaldehyde plus 1-hexanol, and benzyl alcohol plus nonanal were repellent to males at a statistically equivalent level. Similarly the binary blends of benzaldehyde plus nonanal, and benzaldehyde plus 1-hexanol were repellent to females at a statistically equivalent level. Therefore, there is considerable redundancy expressed in which one component may replace another in a binary composition without loss of repellency.

EXAMPLE 4

Experiment 3 followed the same experimental protocol at the same location as Experiments 1 and 2. It was conducted from Jul. 26 to Aug. 3, 1995, and had 10 replicates in which benzyl alcohol, benzaldehyde, nonanal and 1-hexanol were tested in all four possible ternary combinations and in quarternary combination for their ability to disrupt response by the mountain pine beetle to multiple-funnel traps baited with trans-verbenol, exo-brevicomin and myrcene.

Figure 3:
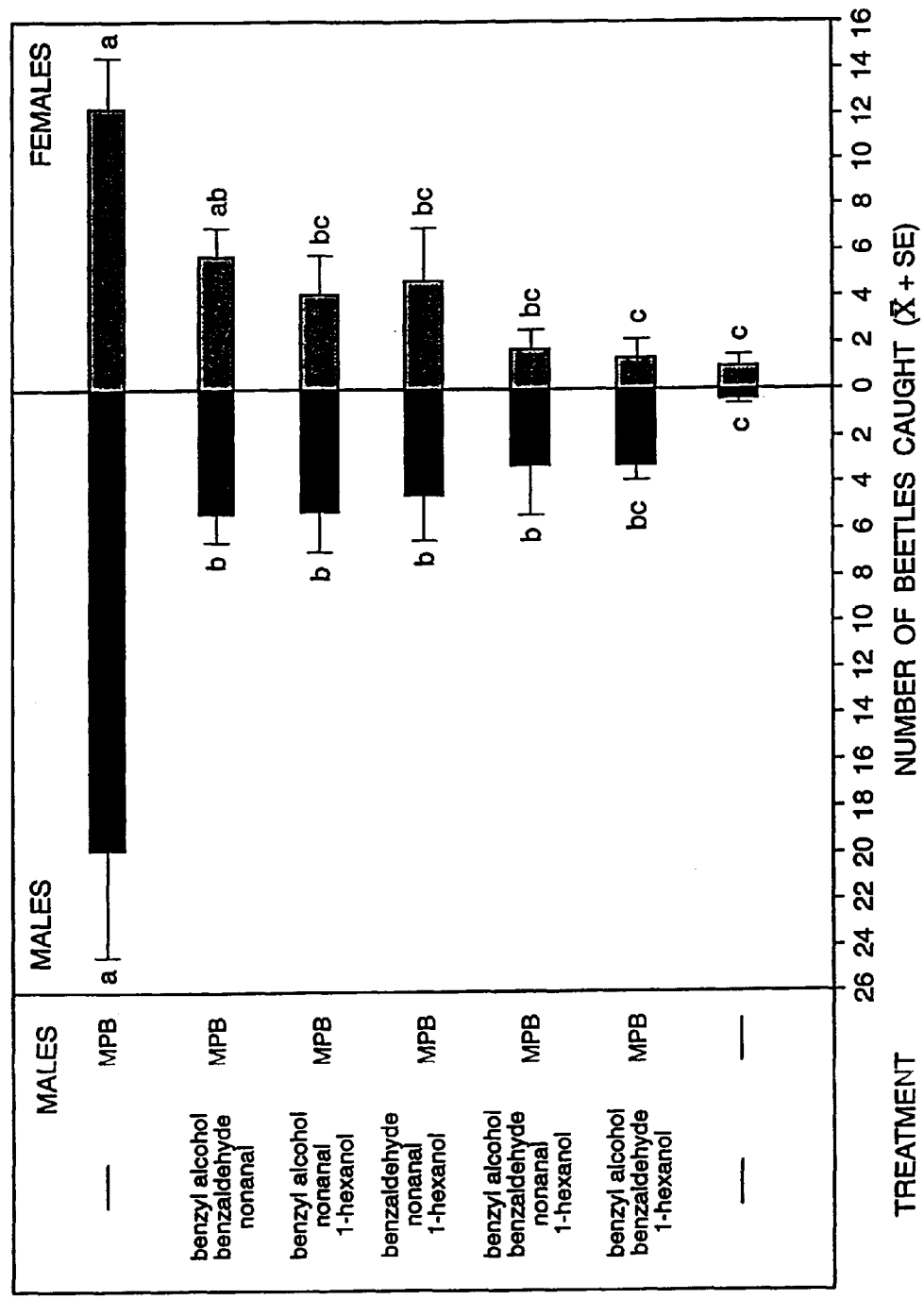
FIG. 3 illustrates a plot of the results of a third experiment showing the numbers of male and female mountain pine beetles captured in multiple-funnel traps baited with the attractant blend of exo-brevicomin, trans-verbenol and myrcene alone or in combination with three non-host volatiles and the green leaf volatile, 1-hexanol, in all possible ternary combinations and in quaternary combination. Willis Creek, near Princeton, B.C., July 26–August 1995, n=10. Data transformed by $\log_{10}$ (x+1) and analyzed by ANOVA and the REGW test. Bars within a sex associated with the same letter are not significantly different, P<0.05. Horizontal lines in the treatment columns indicate no treatment.

FIG. 3 illustrates a plot of the results of a third experiment showing the numbers of male and female mountain pine beetles captured in multiple-funnel traps baited with the attractant blend of exo-brevicomin, trans-verbenol and myrcene alone or in combination with three non-host volatiles and the green leaf volatile, 1-hexanol, in all possible ternary combinations and in quaternary combination. Willis Creek, near Princeton, B.C., July 26–August, 1995, n=10. Data transformed by $\log_{10}$ (x+1) and analyzed by ANOVA and the REGW test. Bars within a sex associated with the same letter are not significantly different, P<0.05. Horizontal lines in the treatment columns indicate no treatment.

As shown in FIG. 3, all four of the ternary blends for male mountain pine beetles, and all but one for females caused significant reductions in trap catches, a further demonstration of redundancy between the disruptive components. The significant disruptive effect for males caused by the blend of benzyl alcohol plus benzaldehyde plus nonanal constitutes additional evidence that these chemicals are new repellents for conifer-infesting bark beetles. The ternary blend of 1-hexanol plus benzaldehyde plus nonanal caused approximately 84% and 88% disruption of trap catches for males and females, respectively. Because the effect was much stronger than that caused by 1-hexanol alone in Experiment 1, this result constitutes additional evidence for the interaction between the green leaf volatile, 1-hexanol, and the two new repellents.

EXAMPLE 5

Experiment 4 followed the same experimental protocol at the same location as Experiments 1–3. It was conducted from Aug. 16–31, 1995, and had 10 replicates in which the quarternary blend of benzyl alcohol plus benzaldehyde plus nonanal plus 1-hexanol, and the antiaggregation pheromone, verbenone (release rate 0.6 mg per 24 h at 22° C.), or both together, were tested for their ability to disrupt response by the mountain pine beetle to multiple-funnel traps baited with trans-verbenol, exo-brevicomin and myrcene.

Figure 4:
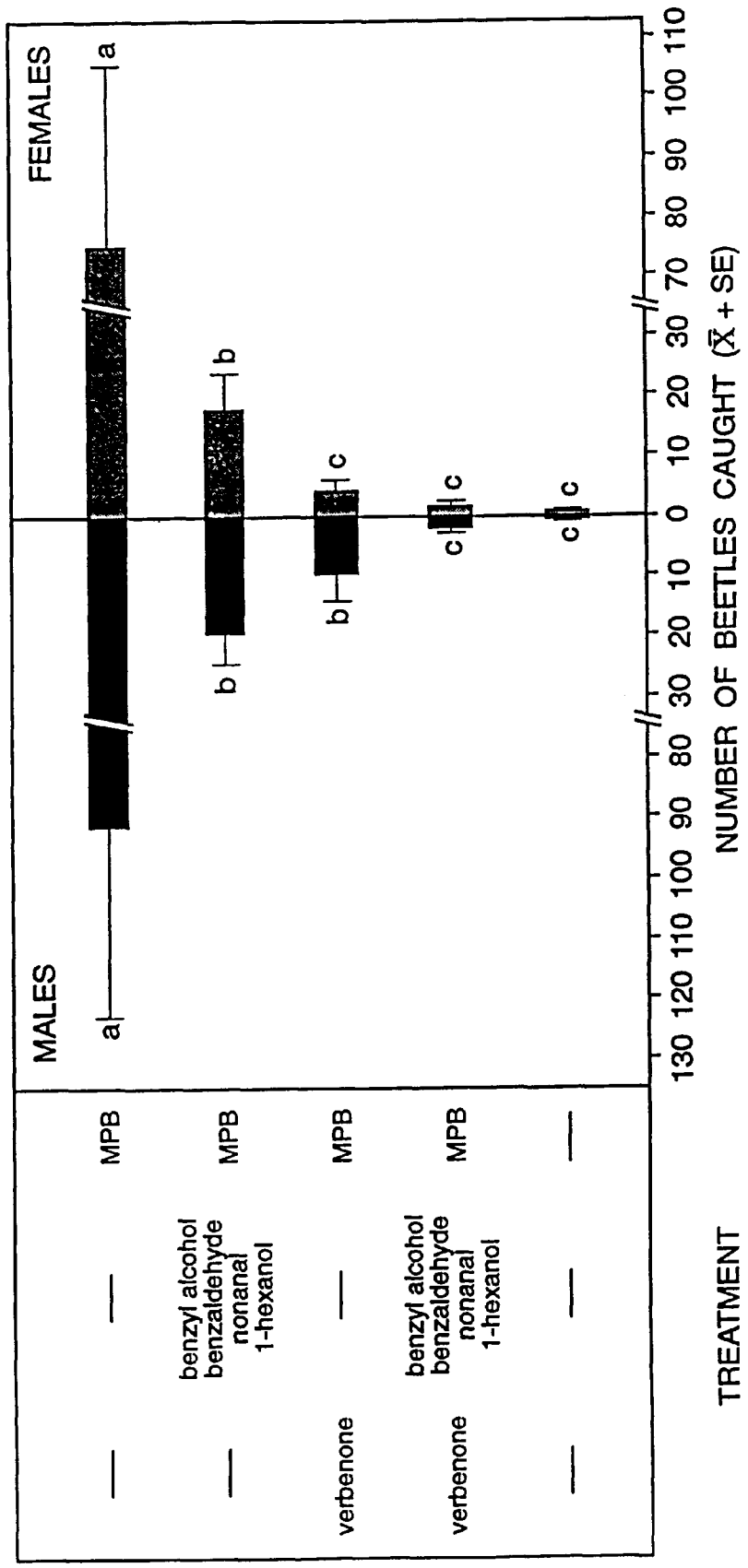
FIG. 4 illustrates a plot of the results of a fourth experiment showing the numbers of male and female mountain pine beetles captured in multiple-funnel traps baited with the attractant blend of exo-brevicomin, trans-verbenol and myrcene alone or in combination with verbenone, a non-host volatile blend consisting of benzyl alcohol, benzaldehyde and nonanal with the green leaf volatile, 1-hexanol, or all repellents together. Willis Creek, near Princeton, B.C., Aug. 16–31, 1995, n=10. Data transformed by $\log_{10}$ (x+1) and analyzed by ANOVA and the REGW test. Bars within a sex associated with the same letter are not significantly different, P<0.05. Horizontal lines in the treatment columns indicate no treatment.

FIG. 4 illustrates a plot of the results of a fourth experiment showing the numbers of male and female mountain pine beetles captured in multiple-funnel traps baited with the attractant blend of exo-brevicomin, trans-verbenol and myrcene alone or in combination with verbenone, a non-host volatile blend consisting of benzyl alcohol, benzaldehyde and nonanal with the green leaf volatile, 1-hexanol, or all repellents together. Willis Creek, near Princeton, B.C., Aug. 16–31, 1995, n=10. Data transformed by $\log_{10}$ (x+1) and analyzed by ANOVA and the REGW test. Bars within a sex associated with the same letter are not significantly different, P<0.05. Horizontal lines in the treatment columns indicate no treatment.

As shown in FIG. 4, both the quarternary blend of non-host angiosperm bark volatiles and verbenone had a highly significant disruptive effect on the response of both sexes of mountain pine beetles to attractant-baited traps. Unexpectedly, the composition comprised of the three non-host volatiles plus 1-hexanol plus verbenone, had an even greater impact, approximately 98% repellency for both sexes. This result indicates that combinations of non-host angiosperm bark volatiles with green leaf volatiles and antiaggregation pheromones can have a greater repellent effect than either type of constituent alone.

EXAMPLE 6

Experiment 5, repeated the treatments in Experiment 4, but challenged mountain pine beetles to attack trees baited with tree baits (Phero Tech Inc.) comprised of trans-verbenol and exo-brevicomin (Borden et al. 1993). Fifty trees (10 replicates of five treatments) (all trees $\geq$20 cm diam. at 1.3 m height) were selected at 25 m intervals on transects through a mountain pine beetle-infested lodgepole pine stand in the valley of Wolfe Creek, 18 km south of Princeton, B.C. Release devices for both attractive baits and candidate disruptants were affixed at least 2 m high in a cluster on the north face of the trees on Jul. 19, 1995. All trees were checked for attack on August 10. If attack occurred, attack density was determined by counting the number of attacks, as evidenced by fresh pitch tubes and frass on the bark, in two 20×40 cm frames (0.16 cm$^2$) at eye level on the east and west faces of the tree. Attack densities were transformed by log10 (x+1) to satisfy assumptions of normality and homogeneity of variance, and then analyzed by ANOVA and the REGW multiple range test ($\alpha$=0.05).

When the trees were checked on August 10, 22 days after treatment, all but one of those on which verbenone was added to the tree baits were attacked (Table 2). Four trees bearing the blend of three non-host bark volatiles plus 1-hexanol remained unattached, as did five treated with the above quarternary blend plus verbenone. Trees with the latter treatment had significantly lower attack densities than trees treated with tree baits alone, all 10 of which were mass attacked.

TABLE 11

Attack by mountain pine beetles on attractant-baited lodgepole pines treated with bubble cap devices releasing the antiaggregation pheromone verbenone, four non-host volatiles or the combination of verbenone and non-host volatiles. Willis Creek, near Princeton, British Columbia, July 19–August 10, 1995.

| Treatment (n = 10)[a] | Number of trees attacked | Attack density per m$^2$ (mean ± SE)[b] |
|---|---|---|
| MPB | 10 | 78.8 ± 7.8 a |
| MPB + verbenone | 9 | 66.3 ± 17.4 ab |
| MPB + benzyl alcohol, benzaldehyde, nonanal, and 1-hexanol | 6 | 38.1 ± 13.6 abc |
| MPB + verbenone + benzyl alcohol, benzaldehyde, nonanal, and 1-hexanol | 5 | 25.6 ± 13.2 bc |
| Unbaited control | 2 | 6.3 ± 5.6 c |

[a]MPB = attractant bait composed of exo-brevicomin and trans-verbenol
[b]Data transformed by log$_{10}$ (x + 1) and analyzed by ANOVA and the REGW test.
Means followed by the same letter are not significantly different, P < 0.05.

These results show that the composition made up of new non-host bark volatile disruptants (benzyl alcohol, benzaldehyde and nonanal), together with a green leaf volatile (1-hexanol) and an antiaggregation pheromone (verbenone) can be used to protect coniferous trees from attack by bark beetles.

EXAMPLE 7

Experiment 6 tested the ability of a blend of 13 antennally active volatiles for the mountain pine beetle (Table I) to protect lodgepole pines from attack. The composition, with percents by volume approximating those found naturally in the bark of non-host angiosperm trees was made up as follows: (E)-2-hexenal (0.4%), hexanal (4.5%), 3-hexanone (0.9%), $\alpha$-pinene (0.6%), 1-hexanol (12.3%), $\beta$-pinene (0.8%), 3-carene (0.4%), limonene (10.3%), benzaldehyde (1.4%), nonanal (4.0%), salicylaldehyde (22.9%), guiacol (20.0)%) and benzyl alcohol (21.6%). Ninety five trees (19 replicates of five treatments) (all trees $\geq$20 cm diam. at 1.3 m height) were selected at 50 m intervals on transects through a mountain pine beetle-infested lodgepole pine stand in the valley of Wolfe Creek, 18 km south of Princeton, B.C. Release devices were affixed at least 2 m high on the north face of the trees on Jul. 25, 1997, with the following treatments: unbaited controls, attractant bait composed of exo-brevicomin and trans-verbenol; attractant bait plus verbenone (bubble cap, release rate 0.6 mg per 24 h); attractant bait plus non-host volatile blend (polyethylene bottle, release rate approximately 70 mg per 24 h at 28° C.) and; attractant bait plus verbenone plus non-host volatile blend. On August 1, 8 and 18 and September 3 and 30, all trees were checked for attack, as evidenced by fresh pitch tubes and frass on the bark. Proportions of trees attacked by the mountain pine beetle were compared by chi square tests adapted for multiple proportions.

Figure 5:
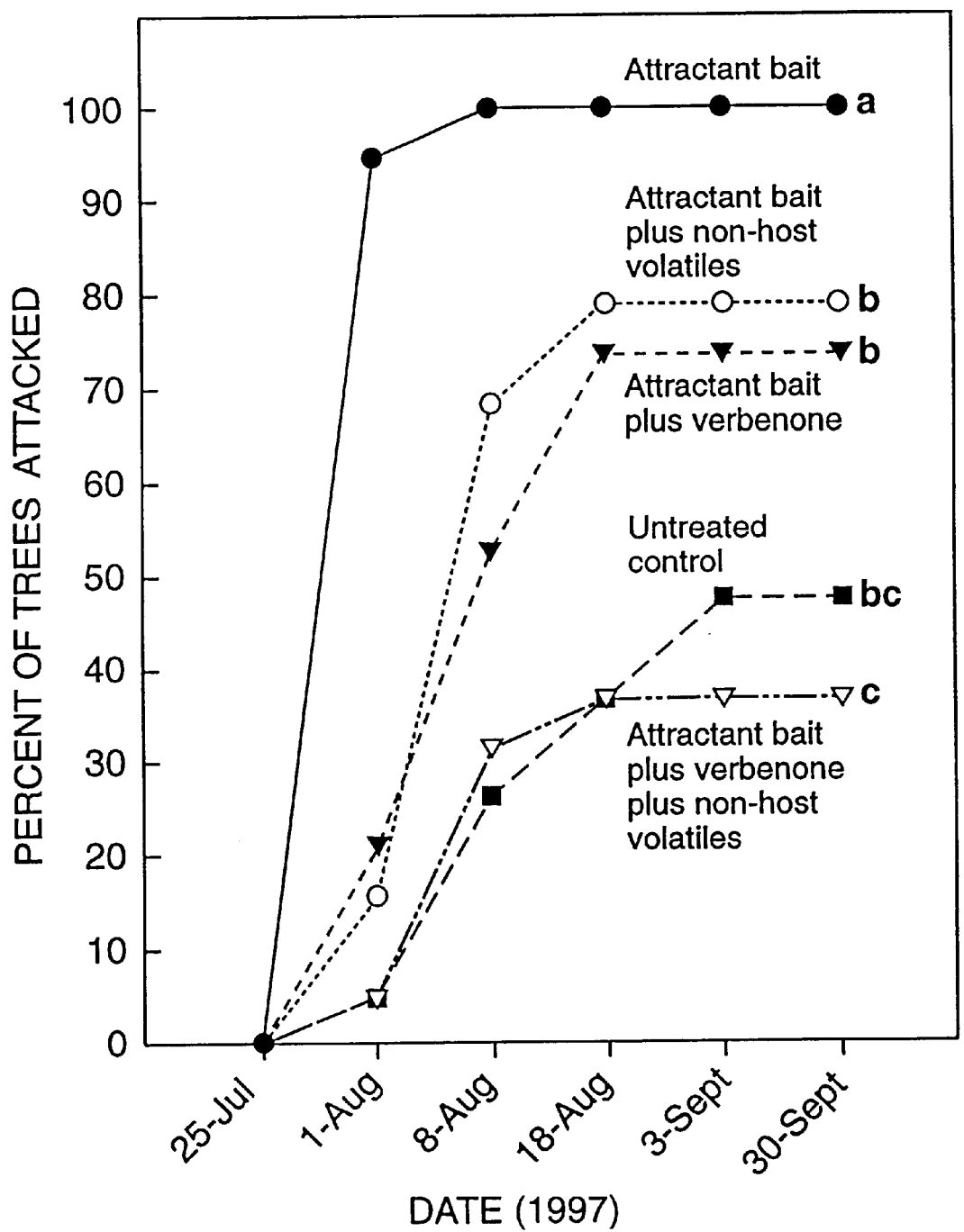
FIG. 5 illustrates a plot of the results of a sixth experiment showing percentages of lodgepole pine trees attacked by the mountain pine beetle on five successive dates following baiting with the attractant blend of exo-brevicomin, trans-verbenol alone or with verbenone, a non-host volatile blend (including three green leaf volatiles), or both verbenone and the non-host volatile blend. Wolfe Creek, near Princeton, B.C., n=10. Lines with the same letter are not significantly different, chi-square test for multiple proportions, P<0.05.

FIG. 5 illustrates a plot of the results of a sixth experiment showing percentages of lodgepole pine trees attacked by the mountain pine beetle on five successive dates following baiting with the attractant blend of exo-brevicomin, trans-verbenol alone or with verbenone, a non-host volatile blend (including three green leaf volatiles), or both verbenone and the non-host volatile blend. Wolfe Creek, near Princeton, B.C., n=10. Lines with the same letter are not significantly different, chi-square test for multiple proportions, P<0.05.

All trees treated with the aggregation pheromones trans-verbenol and exo-brevicomin were attacked by August 8 (FIG. 5). Attack on attractant-baited trees treated with the non-host volatile blend or with verbenone occurred more slowly than for attractant-baited trees, and eventually rose to a level of approximately 75%, significantly lower than that on attractant-baited trees. The lowest attack, lower even than on unbaited trees, was on attractant-baited trees treated with the non-host volatile blend plus verbenone.

These results further demonstrate the disruptant effect on attack by conifer-infesting bark beetles of a new blend made up of benzyl alcohol, benzaldehyde, nonanal, 3-hexanone, salicylaldehyde and guiacol, four monoterpenes and three green leaf volatiles. They also demonstrate increased repellency of a new composition that combines the above non-host volatile blend with the antiaggregation pheromone, verbenone.

EXAMPLE 8

Experiments 7 and 8 were conducted to follow up the unexpected discovery in the bark volatiles of bigleaf maple, trembling aspen, black cottonwood and paper birch of conophthorin as an antennally-active compound for conifer-infesting bark beetles (TABLE I). Both experiments utilized multiple-funnel traps deployed in randomized complete blocks as in Experiments 1–4. Experiment 7 tested responses by the Douglas-fir beetle. It was set up at Lalluwissen Creek, 16 km north of Lytton, B.C. from May 15–20, 1997, and comprised 12 replicates of the following treatments: unbaited traps; attractant bait (Phero Tech Inc.) releasing the host tree monoterpene, α-pinene, at 1.5 mg per 24 h and the aggregation pheromones, frontalin and MCOL at 2.6 mg and 2.0 mg per 24 h, respectively; and the attractant bait plus conophthorin released from a polyethylene microcentrifuge tube cap at 0.3 mg per 24 h. Experiment 8 against the mountain pine beetle was set up from Jul. 18–23, 1997 in the same location as Experiments 1–4, and comprised the following treatments: unbaited traps, attractant-baited traps releasing trans-verbenol, exo-brevicomin and myrcene; conophthorin alone; and attractant-baited traps also releasing conophthorin. Otherwise, experimental protocol and statistical analysis were as in Experiments 1–4.

Conophthorin caused a significant disruption of both sexes of Douglas-fir beetles and mountain pine beetles to attractant-baited traps (TABLE III). Neither species responded to conophthorin alone.

TABLE III

Numbers of male and female Douglas-fir beetles (Experiment 1, n = 12) and mountain pine beetles (Experiment 2, n = 10) captured in multiple-funnel traps baited with attractant baits alone or with conophthorin.

| Expermient No. | Treatment[a] | Number of beetles captured (mean ± SE)[b] | |
|---|---|---|---|
| | | Males | Females |
| Experiment 1 | Unbaited traps | 0.3 ± 0.2 c | 0.8 ± 0.3 c |
| | DFB | 39.0 ± 5.8 a | 23.2 ± 2.9 a |
| | DFB + conophthorin | 23.7 ± 2.0 b | 16.3 ± 2.4 b |
| Experiment 2 | Unbaited traps | 0.0 ± 0.0 c | 0.0 ± 0.0 c |
| | MPB | 20.9 ± 4.5 a | 16.1 ± 6.1 a |
| | Conophthorin | 0.0 ± 0.0 c | 0.0 ± 0.0 c |
| | MPB + conophthorin | 9.1 ± 0.9 b | 9.2 ± 1.5 b |

DFB = attractant bait composed of α-pinene, frontalin and sendenol.
MPB = attractant bait composed of myrcene, trans-verbenol and exo-brevicomin.
[b] Means within a colunm and experiment followed by the same letter are not significantly different, REGW test, P < 0.05.

These results demonstrate that conophthorin is a new repellent for conifer-infesting bark beetles.

EXAMPLE 9

This example reinforces Example 8. It confirms the effect demonstrated in Example 8 on Douglas-fir beetle, *Dendroctonus pseudotsugae* and broadens the effect to beetles in two other genera, *Dryocoetes confusus* and *Ips pini*.

Experiments 9, 10 and 11 were conducted to test the dose response to conophthorin of three different species of conifer-infesting bark beetles in three genera (Douglas-fir beetle, *Dendroctonus pseudotsugae*, western balsam bark beetle, *Dryocoetes confusus* and pine engraver, *Ips pini*) to conophthorin. All three experiments utilized 12-unit multiple funnel traps set up in beetle infested areas in randomized complete blocks as described in Experiments 1–4. All three experiments had the following treatments: unbaited trap, attractant baited trap, attractant bait plus conophthorin released from a polyethylene microcentrifuge tube at 0.3 mg/24 h, and attractant bait plus conophthorin released from a polyethylene microcentrifuge tube at 3 mg/24 h. All attractant baits were supplied by Phero Tech Inc. The attractant bait for the Douglas-fir beetle was ethanol released at about 40 mg/24 h, MCOL (1-methyl-2-cyclohexenol) released at 2.0 mg/24 h and frontalin released at 2.6 mg/24 h. The attractant bait for western balsam bark beetle was a 9:2 blend of (+)-exo-brevicomin and (+)-endo-brevicomin released at 0.3 mg/24 h. The attractant bait for the pine engraver was racemic ipsdienol released at 100 μg/24 h and lanierone (2-hydroxy-4,4,6-trimethyl-2,5-cyclohexadien-1-one) released at 10μ/24 h. Experiment 9 was set up at Lalluwissen Creek, about 16 km north of Lytton, British Columbia, April 29–May 1, 1998. Experiment 10 was set up near Brookmere, British Columbia, Jul. 4–10, 1998. Experiment 11 was set up about 30 km south of Princeton, British Columbia, Aug. 19–26, 1998. Each experiment consisted of about 15 replicates. Otherwise, experimental protocol and statistical analysis were as described in Experiments 1–4.

The 3 mg/24 h conophthorin treatment caused significant disruption of response to attractant baits by both sexes of the Douglas-fir beetle and the pine engraver and females of the western bark beetle (Table IV). Also, in each case, there was evidence of a dose-response relationship, as the lower dose of conophthorin (0.3 mg/24 h) caused a non-significant reduction in the mean number of beetles caught per trap compared to the attractant bait.

These results demonstrate the efficacy of conophthorin alone as a repellent for a variety of genera of conifer-infesting bark beetles and further highlight the potential of this invention to be used in various tree-protection technologies.

TABLE IV

Mean trap catches of three species of conifer-infesting bark beetles in multiple-funnel traps in experiments meant to test the bioactivity of conophthorin in two doses on beetle responses to attractive baits.

| Treatment[a] | Number of beetles captured (mean ± SE)[b] | |
|---|---|---|
| | Males | Females |
| Experiment 9 | | |
| DFB | 30.5 ± 8.5 a | 41.1 ± 10.2 a |
| DFB + 0.3 mg/24 h Conophthorin | 23.0 ± 5.9 a | 33.5 ± 7.3 a |
| DFB + 3 mg/24 h Conophthorin | 11.6 ± 2.1 b | 16.9 ± 2.9 b |
| Blank | 0.1 ± 0.1 c | 0.1 ± 0.1 c |
| Experiment 10 | | |
| WBBB | 0.8 ± 0.3 a | 2.7 ± 0.6 a |
| WBBB + 0.3 mg/24 h Conophthorin | 1.0 ± 0.3 a | 2.1 ± 0.6 ab |
| WBBB + 3 mg/24 h Conophthorin | 0.2 ± 0.2 a | 1.1 ± 0.4 b |
| Blank | 0.2 ± 0.1 a | 0.1 ± 0.1 c |
| Experiment 11 | | |
| PE | 15.7 ± 3.9 a | 26.3 ± 6.5 a |
| PE + 0.3 mg/24 h Conophthorin | 12.8 ± 4.1 ab | 18.7 ± 5.2 ab |
| PE + 3 mg/24 h Conoophthorin | 9.8 ± 3.1 b | 16.0 ± 4.8 b |
| Blank | 0.1 ± 0.1 c | 0.0 ± 0.0 c |

[a]DFB = attractant bait composed of ethanol, frontalin, and MCOL.
WBBB = attractant bait composed of 9:2 (+)-exo-brevicomin: (+)-endo-brevicomin.
PE = attractant bait composed of 1:1 (±)-ipsdienol and lanierone.
[b]Means within an experiment and sex followed by the same letter are not significantly different, REGW test, P < 0.05.

EXAMPLE 10

Example 10 sets forth compounds that have been tested against an attractant bait for ability to protect lodgepole pines from attack by the mountain pine beetle, *Dendroctonus ponderosae*. The data in this example confirm and expand on the data in Example 7, wherein all non-host volatiles, including green leaf volatiles were released in one huge composition. In Example 10, the blends or agents separated.

Experiment 12 compared the efficacy in repelling mountain pine beetles, *Dendroctonus ponderosae,* from attractant baited trees of three agents tested alone and all three together. The agents were: (1) two green leaf volatiles known to be repellent to the mountain pine beetle, (E)-2-hexen-1-ol and (Z)-3-hexen-1-ol; (2) a known mountain pine beetle antiaggregant, verbenone; and (3) a non-host volatile blend comprised of benzyl alcohol, conophthorin, guaiacol, benzaldehyde, salicylaldehyde, and nonanal. Experiment 13 tested the efficacy of binary compositions of the above agents, as well as all three together in repelling mountain pine beetles from attractant baited trees.

Experiment 12 consisted of six treatments: an unbaited control, an attractant bait, bait plus verbenone, bait plus the two green leaf volatiles, bait plus the non-host volatile blend, and bait plus verbenone plus the two green leaf volatiles plus the non-host volatile blend. The attractant bait was composed of an exo-brevicomin flex lure (280 µg/24 h) and a trans-verbenol bubble cap (1.5 mg/24 h) (Phero Tech, Inc., Delta, British Columbia). Verbenone was released from a bubble cap at 1 mg/24 h. (E)-2-hexen-1-ol and (Z)-3-hexen-1-ol were released from separate bubble caps, each at 3.8 mg/24 h. Release devices and rates for the non-host blend were: benzyl alcohol (3.5 mg/24 h) in a bubble cap, conophthorin (3 mg/24 h) in a polyethylene microcentrifuge tube, and a blend of salicylaldehyde, benzaldehyde, nonanal, and guaiacol in a 15 ml polyethylene bottle with approximate release rates of 1.5, 1.7, 1.0, and 2.0 mg/24 h respectively. One hundred and nineteen trees (20 replicates of 5 treatments and 19 replicates of the unbaited treatment) (all trees >19 cm in diameter at 1.3 m height) were selected at 33 m intervals on east/west transects in the Whipsaw Creek valley about 20 km south of Princeton, British Columbia. The stand utilized for the experiment was heavily infested with the mountain pine beetle. Treatments were stapled to trees, on the bole, at least 2 m high on the north side on Jul. 15, 1998. Trees were assessed for attack (evidenced by frass and pitch tubes) on July 29, August 12–26. Pitch tubes and entrance holes were counted on the east and west sides of the treatment trees in a 20×40 cm rectangle on each side. If the sum of the pitch tubes and entrance holes in the two rectangles was ≧5, the tree was designated as mass attacked. Statistical analysis of proportions of trees mass attacked by mountain pine beetle was performed as described in Experiment 6, with $\alpha=0.05$.

Experiment 13 was conducted and analysed exactly as in Experiment 12, with the following exceptions. The six treatments were an unbaited control, an attractant bait, bait plus verbenone plus the non-host volatile blend, bait plus the two green leaf volatiles plus the non-host volatile blend, bait plus verbenone plus the two green leaf volatiles, and bait plus verbenone plus the two green leaf volatiles plus the non-host volatile blend. The experiment consisted of 18 repetitions of each treatment (108 trees). The experiment was set up on Jul. 22, 1998 and assessed on August 5, August 19, September 2. All trees were >20 cm diameter at 1.3 m height.

Figure 6:
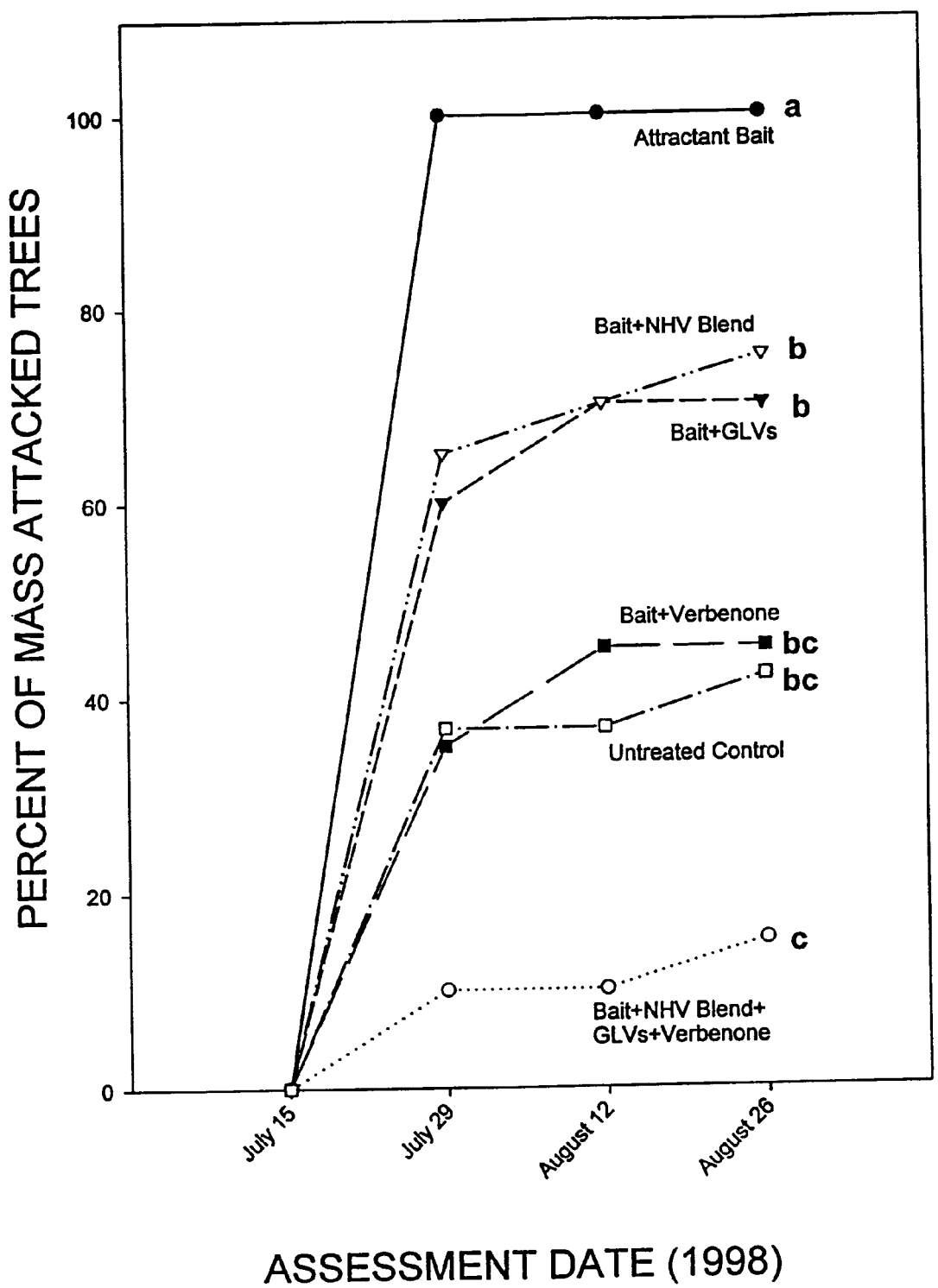
FIG. 6 illustrates the results of Experiment 12 showing percentages of lodgepole pine trees mass attacked by the mountain pine beetle on three successive dates following baiting with the attractant blend of exo-brevicomin and trans-verbenol alone, and with: (1) a blend of two green leaf alcohols [(E)-2-hexen-1-ol and (Z)-3-hexen-1-ol]; (2) verbenone; (3) a non-host volatile blend [benzyl alcohol, conophthorin, guaiacol, benzaldehyde, nonanal, and salicylaldehyde]; or (4) the green leaf alcohols, verbenone, and the non-host volatile blend all together. Whipsaw Creek, near Princeton, British Columbia, n=20. Lines with the same letter are not significantly different, chi-square test for multiple proportions, P<0.05.

In experiment 12, all attractant baited trees were mass attacked by July 29, the time of the first assessment (FIG. 6). Between 70%–75% of the trees in the treatments bait plus non-host blend and bait plus green leaf volatiles were attacked by August 26, the time of the final assessment. About 40% of untreated trees and trees with bait plus verbenone were mass attacked by the time of the final assessment. Only 15% of the trees with the bait plus all three components were mass attacked at the final assessment. Therefore each composition separately disrupted attraction to the attractant baited trees, but the aggregate composition of all three components almost completely eliminated attack.

Figure 7:
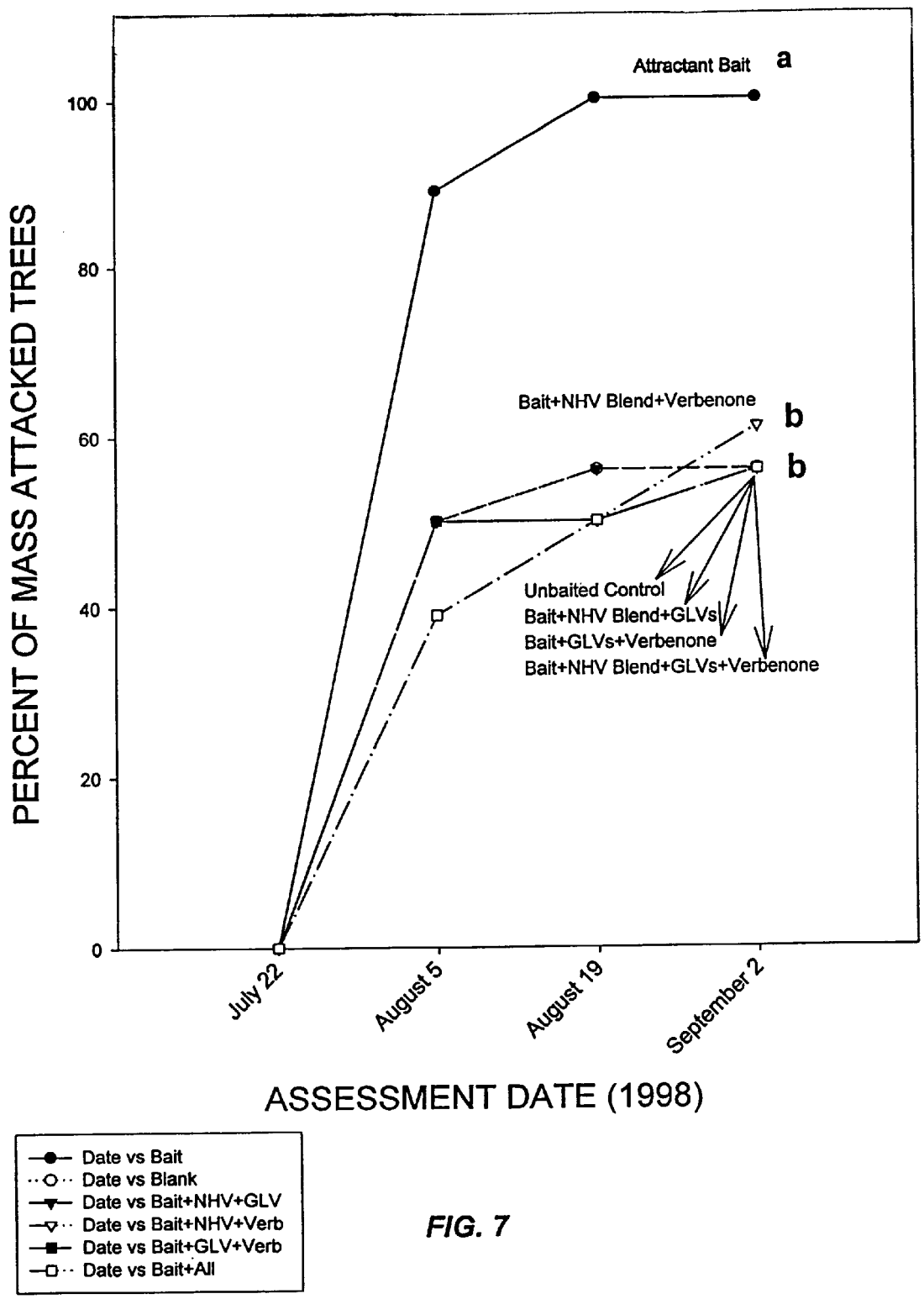
FIG. 7 illustrates the results of Experiment 13 showing percentages of lodgepole pine trees attacked by the mountain pine beetle on three successive dates following baiting with the attractant blend of exo-brevicomin and trans-verbenol alone, and with all possible binary compositions and the ternary composition of: (1) a blend of two green leaf alcohols [(E)-2-hexen-1-ol and (Z)-3-hexen-1-ol]; (2) verbenone; and (3) a non-host volatile blend [benzyl alcohol, conophthorin, guaiacol, benzaldehyde, nonanal, and salicylaldehyde]. Whipsaw Creek, near Princeton, British Columbia, n=18. Lines with the same letter are not significantly different, chi-square test for multiple proportions, P<0.05.

In experiment 13, all attractant-baited trees were mass attacked by August 19, the time of the second assessment (FIG. 7). At that point between 55% and 61% of trees in all other treatments were mass attacked. These proportions of attack remained essentially the same by September 2. All trees with repellent treatments were mass attacked in significantly lower proportion than the attractant-baited trees and none of the repellent treatments was statistically different from the unbaited control treatment.

The result of experiments 12 and 13 highlight two important points. First, experiment 12 shows that a blend of non-host volatiles excluding green leaf volatiles is effective alone at reducing mountain pine beetle attack on baited trees. Second, both experiments show that any of the binary blends, or the ternary blend, of green leaf volatiles, other non-host volatiles, and verbenone are more powerful compositions for repelling mountain pine beetles than any of the three components alone.

EXAMPLE 11

Examples 11 and 12 overlap and expand on Examples 1–6. Non-host volatiles were separated into three groups and tested alone, in all possible binary blends and in the ternary blend against the Douglas-fir beetle (Example 11) and the mountain pine beetle (Example 12).

Experiment 14 tested the efficacy of three groups of non-host volatiles at repelling Douglas-fir beetles, *Dendroctonus pseudotsugae,* from attractant baited traps. Experiment 15 tested the efficacy of the same three groups of non-host volatiles in binary compositions at repelling Douglas-fir beetles. Both experiments also tested all three groups in a ternary composition for efficacy as a repellent against the beetle.

Compounds, with release rates, were grouped into groups 1–3 for testing as follows:

GROUP 1: the green leaf volatiles, 1-hexanol (2.8 mg/24 h), (Z)-3-hexen-1-ol (3.7 mg/24 h), hexanal (8.2 mg/24 h), and (E)-2-hexenal (34 mg/24 h), in a blend released from a 15 ml polyethylene bottle;

GROUP 2: benzyl alcohol (3.5 mg/24 h) in a bubble cap, conophthorin (3 mg/24 h) in a polyethylene microcentrifuge tube, and a blend of salicylaldehyde, benzaldehyde, nonanal, and guaiacol in a 15 ml polyethylene bottle with approximate release rates of 1.5, 1.7, 1.0, and 2 mg/24 h respectively; and GROUP 3: heptanal (4 mg/24 h), (E)-2-heptenal (3.7 mg/24 h), methyl salicylate (3.6 mg/24 h), decanal (2.5 mg/24 h), 4-allylanisole (3.8 mg/24 h) and nerolidol (0.1 mg/24 h), in a blend released from a 15 ml polyethylene bottle and thymolmethylether (2.7 mg/24 h) in a polyethylene microcentrifuge tube. Attractant baits for Douglas-fir beetle were as described in Example 9.

Experiment 14 consisted of six treatments: an unbaited control, an attractant bait, bait plus group 1, bait plus group 2, bait plus group 3, and bait plus groups 1, 2 and 3. Baits and treatments were hung at mid-level in 12-unit multiple funnel traps. Treatments were allocated to traps in a randomized complete block design, with 15 replicates and traps were each at least 15 m apart. Beetles were collected from the traps and stored at −12° C. until they were counted and sexed. Trap catch data were transformed by $\log_{10}(x+1)$ and were analyzed using SAS software by ANOVA and the Ryan-Einot-Gabriel-Welsch multiple-range test at a=0.05. Experiment 14 was conducted near Lytton, British Columbia, between May 5–7, 1998.

Experiment 15 was conducted and analyzed exactly as was Experiment 14 except for the following differences. The treatments in Experiment 15 were: unbaited control, attractant bait, bait plus groups 1 and 2, bait plus groups 1 and 3, bait plus groups 2 and 3, and bait plus groups 1, 2 and 3. Fifteen replicates were carried out for each treatment except for bait plus groups 1 and 3 and bait plus groups 1–3, which each had 14 replicates. The experiment was conducted between May 7–11, 1998.

Table V outlines the results of Experiments 14 and 15. In Experiment 14, group 1 was shown to be significantly repellent to female Douglas-fir beetles and both group 2 and the composition of groups 1, 2 and 3 together were repellent to both sexes. The latter composition was highly repellent, reducing total mean trap catches to about 12% of the level of the attractant baited traps.

In Experiment 15, all binary compositions and the ternary composition were shown to be repellent to both sexes of Douglas-fir beetle.

These results extend the efficacy of our invention to the Douglas-fir beetle and highlight the powerful repellent effect of these chemicals, in combination, against conifer-infesting bark beetles. In particular, in Experiment 14, there was a significant repellency imparted by group 2 alone, and significantly greater repellency of the composition containing green leaf volatiles in combination with other non-host volatiles than there was for any of the three groups alone.

TABLE IV

Mean trap catches of the Douglas-fir beetle in response to attractant baits and three groups of non-host volatiles.

| Treatment[a] | Mean trap catch ± SE[a] | |
|---|---|---|
| | Males | Females |
| Experiment 14 | | |
| Attractant Bait | 27.5 ± 6.4 a | 48.4 ± 7.9 a |
| Bait + Group 3 | 23.0 ± 8.5 a | 33.6 ± 8.2 ab |
| Bait + Group 1 | 15.7 ± 2.8 a | 26.6 ± 5.5 b |
| Bait + Group 2 | 12.1 ± 5.7 b | 13.5 ± 3.4 c |
| Bait + All Three Groups | 3.7 ± 1.9 c | 5.4 ± 2.4 d |
| Blank | 0.1 ± 0.1 d | 0.8 ± 0.4 e |
| Experiment 15 | | |
| Attractant Bait | 19.9 ± 4.8 a | 44.6 ± 9.1 a |
| Bait + Group 1 + Group 3 | 10.7 ± 3.9 b | 20.6 ± 7.0 b |
| Bait + Group 1 + Group 2 | 4.3 ± 1.5 c | 9.6 ± 3.2 c |
| Bait + All Three Groups | 2.9 ± 1.7 c | 6.6 ± 3.6 c |
| Bait + Group 2 + Group 3 | 1.8 ± 0.6 c | 5.0 ± 1.7 c |
| Blank | 0.3 ± 0.1 d | 0.7 ± 0.5 d |

[a]Means within an experiment and sex followed by the same letter are not significantly different, REGW test, $P < 0.05$.

EXAMPLE 12

Experiments 16 and 17 tested the efficacy of non-host volatiles against the mountain pine beetle, *Dendroctonus ponderosae,* and were otherwise identical in purpose and method to Experiments 14 and 15 of Example 11, except for the following differences.

The experiments were carried out in the Whipsaw Creek valley, about 20 km south of Princeton, British Columbia, between July 14–21, 1998 (Experiment 16) and Jul. 21–27, 1998 (Experiment 17). The attractant bait consisted of trans-verbenol (1.5 mg/24 h), exo-brevicomin (280 μg/24 h), and myrcene (95 mg/24 h). The number of replicates of each treatment varied from 10 to 15, as outlined in Table VI. Beetles were not sexed due to extensive damage to trap catches caused by captured insect predators.

In Experiment 16, group 1 significantly repelled mountain pine beetles, as did the mixture of all three groups (Table VI). In Experiment 17, all binary compositions were repellent to mountain pine beetles with the composition of all three groups again performing the best, reducing total mean trap catches to about 12% of the mean trap catch of the attractant bait.

These experiments further show the efficacy and potential of our invention at repelling conifer-infesting bark beetles, and again show the significant effect of interaction between grean leaf volatiles and other non-host volatiles.

TABLE VI

Mean trap catches of the mountain pine beetle in response to various combinations of non-host volatile chemicals.

| Treatment | n | Mean trap catch ± SE[a] |
|---|---|---|
| Experiment 16 | | |
| Attractant Bait | 12 | 14.3 ± 4.5 a |
| Bait + Group 3 | 12 | 13.4 ± 3.5 a |
| Bait + Group 2 | 10 | 9.9 ± 3.4 ab |
| Bait + Group 1 | 11 | 6.0 ± 2.1 bc |
| Bait + All Three Groups | 13 | 3.6 ± 1.1 c |
| Blank | 12 | 2.2 ± 1.3 d |
| Experiment 17 | | |
| Attractant Bait | 13 | 9.8 ± 1.9 a |
| Bait + Group 1 + Group 3 | 13 | 3.9 ± 1.2 b |
| Bait + Group 2 + Group 3 | 15 | 3.1 ± 0.8 bc |
| Bait + Group 1 + Group 2 | 15 | 1.7 ± 0.4 bc |
| Bait + All Three Groups | 15 | 1.1 ± 0.2 c |
| Blank | 15 | 0.1 ± 0.1 d |

[a]Means within an experiment followed by the same letter are not significantly different, REGW test, $P < 0.05$.

As will be apparent to those skilled in the art in the light of the foregoing discloure, many alterations and modifications are possible in the practice of this invention without departing from the spirit or scope thereof. Accordingly, the scope of the invention is to be construed in accordance with the substance defined by the following claims.

REFERENCES

U.S. PATENT DOCUMENTS

Dickens, J. C., R. F. Billings and T. L. Payne. 1993. Green leaf volatiles as inhibitors of bark beetle aggregation pheromones. U.S. Pat. No. 5,273,996.

Dickens, J. C., R. F. Billings and T. L. Payne. 1995. Green leaf volatiles as inhibitors of bark beetle aggregation pheromones. U.S. Pat. No. 5,468,770.

Hayes, J. L., B. L. Strom, L. Roton and L. L. Ingram. 1995. A repellent of bark beetles for protection to conifers. U.S. Pat. No. 5,403,863.

Hayes, J. L., B. L. Strom, L. Roton and L. L. Ingram. 1996. 4-Allylanisole analog scolytid repellents. U.S. Pat. No. 5,518,757.

Lindgren, B. S., J. H. Borden, M. Gnatowski, P. C. Wong and M. D. McGregor. 1994. Method and composition for controlling mountain pine beetles. U.S. Pat. No. 5,281,418.

OTHER PUBLICATIONS

Amman, G. D., R. W. Thier, M. D. McGregor and R. F. Schmitz. 1989. Efficacy of verbenone in reducing lodgepole pine infestation by mountain pine beetles in Idaho. Can. J. For. Res. 19: 60–64.

Amman, G. D., R. W. Thier, J. C. Weatherby, L. A. Rasmussen and A. S. Munson. 1991. Optimum dosage of verbenone to reduce infestation of mountain pine beetle in lodgepole pine stands of central Idaho. USDA For. Serv. Res. Pap. INT-446.

Bentz, B., C. K. Lister, J. M. Schmid, S. A. Mata, L. A. Rasmussen and D. Haneman. 1989. Does verbenone reduce mountain pine beetle attacks in susceptible stands of ponderosa pine? USDA For. Serv. Res. Note RM-495.

Berisford, C. W., U. E. Brady, C. W. Fatzinger and B. H. Ebel. 1986. Evaluation of a repellent for prevention of attacks by three species of southern pine bark beetles (Coleoptera: Scolytidae). J. Entomol. Sci. 21: 316–318.

Bertram, S. L. and T. D. Paine. 1994a. Response of *Dendroctonus brevicomis* LeConte (Coleoptera: Scolytidae) to different release rates and ratios of aggregation semiochemicals and the inhibitors verbenone and ipsdienol. J. Chem. Ecol. 20: 1617–1629.

Bertram, S. L. and T. D. Paine. 1994b. Influence of aggregation inhibitors (verbenone and ipsdienol) on landing and attack behavior of *Dendroctonus brevicomis* (Coleoptera: Scolytidae) to different release rates and ratios of aggregation semiochemicals and the inhibitors verbenone and ipsdienol. J. Chem. Ecol. 20: 2931–2941.

Birgersson, G., G. L. DeBarr, P. de Groot, M. Dalusky, H. D. Pierce, Jr., J. H. Borden, H. Meyer, W. Francke, K. E. Espelie and C. W. Berisford. 1995. Pheromones in white pine cone beetle, *Conophthorus coniperda* (Schwarz) (Coleoptera: Scolytidae). J. Chem. Ecol. 21: 143–167.

Borden, J. H. 1985. Aggregation pheromones. pp. 257–285. In G. A. Kerkut and L. I. Gilbert (eds.) Comprehensive insect physiology, biochemistry and pharmacology. Vol. 9. Pergammon Press, Oxford.

Borden, J. H. 1996. Disruption of semiochemical-mediated aggregation in bark beetles. pp. 421–438. In R. T. Carde and A. K. Minks (eds.). Insect pheromone research: new directions. Chapman and Hall, New York.

Borden, J. H. and B. S. Lindren. 1988. The role of semiochemicals in IPM of the mountain pine beetle. pp. 247–255. In T. L. Payne and H. Saarenmaa. Integrated control of scolytid bark beetles. Virginia Polytechnic Institute and State Univ., Blacksburg, Va.

Borden, J. H., L. C. Ryker, L. J. Chong, H. D. Pierce, Jr., B. D. Johnston and A. C. Oehlschlager. 1987. Response of the mountain pine beetle, *Dendroctonus ponderosae* Hopkins (Coleoptera: Scolytidae), to five semiochemicals in British Columbia lodgepole pine forests. Can. J. For. Res. 17: 118–128.

Borden, J. H., L. J. Chong and D. J. Bergrinson. 1988. Assessment of two pine oil treatments to protect stands of lodgepole pine from attack by the mountain pine beetle. J. Entomol. Soc. B.C. 85: 28–33.

Borden, J. H., D. R. Devlin and D. R. Miller. 1992. Synomones of two sympatric species deter attack by the pine engraver, Ips pini (Coleoptera: Scolytidae). Can. J. For. Res. 22: 381–387.

Borden, J. H., L. J. Chong, B. S. Lindgren, E. J. Begin, T. M. Ebata, L. E. Maclauchlan and R. S. Hodkinson. 1993. A simplified tree bait for the mountain pine beetle. Can. J. For. Res. 23: 1108–1113.

Byers, J. A. 1989. Chemical ecology of bark beetles. Experientia 45: 271–283.

Devlin, D. R. and J. H. Borden. 1994. Efficacy of antiaggregants for the pine engraver, *Ips pini* (Say) (Coleoptera: Scolytidae). Can. J. For. Res. 24: 2469–2476.

Dickens, J. C., R. F. Billings and T. L. Payne. 1992. Green leaf volatiles interrupt aggregation pheromone response in bark beetles infesting southern pines. Experientia 48: 523–524.

Furniss, M. M., R. W. Clausen, G. P. Markin, M. D. McGregor and R. L. Livington. 1981. Effectiveness of Douglas-fir beetle antiaggregation pheromone applied by helicopter. USDA For. Serv. Gen. Tech. Rep. INT-101.

Furniss, M. M., G. P. Markin and Y. J. Hager. 1982. Aerial applications of Douglas-fir beetle antiaggregative pheromone: equipment and evaluation. USDA For. Serv. Gen. Tech. Rep. INT-137.

Gibson, K. E., R. F. Schmitz, G. D. Amman and R. D. Oakes. 1991. Mountain pine beetle response to different verbenone dosages in pine stands of western Montana. USDA For. Serv. Res. Pap. INT-444.

Gries, G. 1995. Prospects of new semiochemicals and technologies. pp. 44–47. In S. M. Salom and K. R. Hobson (eds.) Application of semiochemicals for management of bark beetle infestations—proceedings of an informal conference. USDA For. Serv. Gen. Tech. Rep. INT-GTR-318.

Hayes, J. L. and B. L. Strom. 1994. 4-Allylanisole as an inhibitor of bark beetle (Coleoptera: Scolytidae) aggregation. J. Econ. Entomol. 87: 1586–1594.

Hayes, J. L., B. L. Strom, L. M. Roton and L. L. Ingram. 1994. Repellent properties of the compound 4-allylanisole to the southern pine beetle. J. Chem. Ecol. 20: 1595–1615.

Hayes, J. L., J. R. Meeker, J. L. Foltz and B. L. Strom. 1996. Suppression of bark beetles and protection of pines in the urban environment: a case study. J. Arboriculture 22: 67–74.

Hobson, K. R. 1995. Host compounds as semiochemicals for bark beetles. pp. 48–51. In S. M. Salom and K. R. Hobson (eds.). Application of semiochemicals for management of bark beetle infestations-proceedings of an informal conference. USDA For. Serv. Gen. Tech. INT-GTR-318.

Kline, L. N., R. F. Schmitz, J. A. Rudinsky and M. M. Furniss. 1974. Repression of spruce beetle (Coleoptera) attraction by methylcyclohexenone in Idaho. Can. Entomol. 106: 485–491.

Kostyk, B. C., J. H. Borden and G. Gries. 1993. Photoisomerism of antiaggregation pheromone verbenone: biological and practical implications with respect to the mountain pine beetle, *Dendroctonus ponderosae* Hopkins (Coleoptera: Scolytidae). J. Chem. Ecol. 19: 1749–1959.

Lindgren, B. S., M. D. McGregor, R. D. Oakes and H. E. Meyer. 1989a. Suppression of spruce beetle attacks by MCH released from bubble caps. West. J. Appl. For. 4: 49–52.

Lindgren, B. S., J. H. Borden, G. H. Cushon, L. J. Chong and C. J. Higgins. 1989b. Reduction of mountain pine beetle (Coleoptera: Scolytidae) attacks by verbenone in lodgepole pine stands in British Columbia. Can. J. For. Res. 19: 65–68.

Lister, C. K., J. M. Schmid, S. A. Mata, D. Haneman, C. O'Neil, J. Pasek and L. Sower. 1990. Verbenone bubble caps ineffective as a preventive strategy against mountain pine beetle attacks in ponderosa pine. USDA For. Serv. Res. Note RM-501.

McGregor, M. D., M. M. Furniss, R. D. Oakes, K. E. Gibson and H. E. Meyer. 1984. MCH pheromone for preventing Douglas-fir beetle infestation in windthrown trees. J. For. 82: 613–616.

McMullen, L. H. and L. Safranyik. 1985. Some effects of pine oil on mountain pine beetle (Coleoptera: Scolytidae) at different population levels. J. Entomol. Soc. B.C. 82: 29–30.

Nijholt, W. W., L. H. McMullen and L. Safranyik. 1981. Pine oil protects living trees from attack by three bark beetle species, Dendroctonus spp. (Coleoptera: Scolytidae). Can. Entomol. 113: 337–340.

O'Donnell, B. P., T. L. Payne and K. D. Walsh. 1986. Effect of pine oil on landing and attack by the southern pine beetle (Coleoptera: Scolytidae). J. Entomol. Sci. 21: 319–321.

Paine, T. D. and C. C. Hanlon. 1991. Response of *Dendroctonus brevicomis* and *Ips paraconfusus* (Coleoptera: Scolytidae) to combinations of synthetic pheromone attractants and inhibitors verbenone and ipsdienol. J. Chem. Ecol. 17: 2163–2176.

Payne, T. L. and R. F. Billings. 1989. Evaluation of (S)-verbenone applications for suppressing southern pine beetle (Coleoptera: Scolytidae) infestations. J. Econ. Entomol. 82: 1702–1708.

Payne, T. L., R. F. Billings, C. W. Berisford, S. M. Salom, D. M. Grossman, M. J. Dalusky and W. W. Upton. 1992. Disruption of *Dendroctonus frontalis* (Coleoptera: Scolytidae) infestations with an inhibitor pheromone. J. Appl. Entomol. 114: 341–347.

Pierce, H. D., Jr., P. de Groot, J. H. Borden, S. Ramaswamy and A. C. Oehlschlager. 1995. Pheromones in red pine cone beetle, *Conophthorus resinosae* Hopkins, and its synonym, *C. banksianae* McPherson (Coleoptera: Scolytidae). J. Chem. Ecol. 21: 169–185.

Richmond, C. E. 1985. Effectiveness of two pine oils for protecting lodgepole pine from attack by the mountain pine beetle (Coleoptera: Scolytidae). Can. Entomol. 117: 1445–1446.

Rudinsky, J. A. 1973. Multiple functions of the Douglas-fir beetle pheromone 3-methyl-2-cyclohexen-1-one. Environ. Entomol. 2: 579–585.

Rudinsky, J. A., C. Sartwell, Jr., T. M. Graves and M. E. Morgan. 1974. Granular formulation of methylcyclohexenone: an antiaggregative pheromone of the Douglas-fir beetle and spruce bark beetles. Z. angew. Entomol. 75: 254–263.

Ryker, L. C. and K. L. Yandell. 1983. Effect of verbenone on aggregation of *Dendroctonus ponderosae* Hopkins (Coleoptera: Scolytidae) to synthetic attractant. Z. angew. Entomol. 96–452–459.

Shea, P. J., M. D. McGregor and G. E. Daterman. 1992. Aerial application of verbenone reduces attack of lodgepole pine by the mountain pine beetle. Can. J. For. Res. 22: 436441.

Strom, B. L., R. A. Goyer and J. L. Hayes. 1995. Naturally occurring compound can protect southern pines from the southern pine beetle. Louisiana Agriculture 38(4): 5–7.

Strom, B. L., L. L. Ingram, J. L. Hayes and R. Goyer. 1996. Variation in concentration of 4-allylanisole in oleoresin of southern pines. USDA For. Serv., S. For. Exp. Sta., SPB Update, October 1996: 2.

Visser, J. H. 1986. Host odor perception in phytophagous insects. Annu. Rev. Entomol. 31: 121–144.

Werner, R. A. 1995. Toxicity and repellency of 4-allylanisole and monoterpenes from white spruce and tamarak to the spruce beetle and eastern larch beetle (Coleoptera: Scolytidae). Environ. Entomol. 24: 372–379.

Werner, R. A., E. H. Hosten and F. L. Hastings. 1986. Evaluation of pine oil for protecting white spruce from spruce beetle (Coleoptera: Scolytidae) attack. J. Entomol. Soc. B.C. 83: 3–5.

Wilson, I. M., J. H. Borden, R. Gries and G. Gries. 1996. Green leaf volatiles as antiaggregants for the mountain pine beetle, *Dendroctonus ponderosae* Hopkins (Coleoptera: Scolytidae). J. Chem. Ecol. 22: 1861–1875.

What is claimed is:

1. A method of repelling conifer-infesting bark beetles from a surface subject to attack by said beetles, comprising treating the surface with a repellent compound selected from the group consisting of one or more of: toluene, pentanol, 2-hexanone, 3-hexanone, heptanal, benzaldehyde, 2-hydroxycyclohexanone, benzyl alcohol, (E)-ocimene, salicylaldehyde, conophthorin, guiacol, nonanal, methylsalicylate, decanal, thymolmethylether, (E)-nerolidol and dendrolasin, or mixture thereof, in amounts sufficient to repel said beetles from said surface, or eluting said compound from inert devices or carriers applied to said surface in amounts sufficient to repel said beetles from said surface from which said beetles are to be repelled.

2. A method of repelling conifer-infesting bark beetles from a surface subject to attack by said beetles, comprising treating the surface with a repellent compound selected from the group consisting of one or more of: heptanal, benzaldehyde, benzyl alcohol, salicylaldehyde, conophthorin, guiacol, nonanal, methylsalicylate, decanal and (E)-nerolidol, or mixture thereof, in amounts sufficient to repel said beetles from said surface, or eluting said compound from inert devices or carriers applied to said surface in amounts sufficient to repel said beetles from said surface from which said beetles are to be repelled.

3. A method of protecting individual logs, trees and groups of coniferous tree hosts from attack by conifer-infesting bark beetles, comprising treating said logs, trees and groups of coniferous tree hosts with a repellent compound selected from the group consisting of: toluene, pentanol, 2-hexanone, 3-hexanone, heptanal, benzaldehyde, 2-hydroxycyclohexanone, benzyl alcohol, (E)-ocimene, salicylaldehyde, conophthorin, guiacol, nonanal, methylsalicylate, decanal, thymolmethylether, (E)-nerolidol and dendrolasin, or mixtures thereof.

4. A method of protecting individual logs, trees and groups of coniferous tree hosts from attack by conifer-infesting bark beetles, comprising treating said logs, trees and groups of coniferous tree hosts with a repellent compound selected from the group consisting of: heptanal, benzaldehyde, benzyl alcohol, salicylaldehyde, conophthorin, guiacol, nonanal, methylsalicylate, decanal and (E)-nerolidol, or mixtures thereof.

5. The method of claim 1 wherein said compound or mixture is combined with a green leaf volatile selected from the group consisting of hexanal, (E)-2-hexenal, 1-hexanol, (E)-2-hexen-1-ol, (Z)-2-hexen-1-ol, and (Z)-3-hexen-1-ol, and mixtures thereof.

6. The method of claim 2 wherein said compound or mixture is combined with a green leaf volatile selected from the group consisting of hexanal, (E)-2-hexenal, 1-hexanol, (E)-2-hexen-1-ol, (Z)-2-hexen-1-ol, and (Z)-3-hexen-1-ol, and mixtures thereof.

7. The method of claim 3 wherein said compound or mixture is combined with a green leaf volatile selected from the group consisting of hexanal, (E)-2-hexenal, 1-hexanol, (E)-2-hexen-1-ol, (Z)-2-hexen-1-ol, and (Z)-3-hexen-1-ol, and mixtures thereof.

8. The method of claim 4 wherein said compound or mixture is combined with a green leaf volatile selected from the group consisting of hexanal, (E)-2-hexenal, 1-hexanol, (h)-2-hexen-1-ol, (Z)-2-hexen-1-ol, and (Z)-3-hexen-1-ol, and mixtures thereof.

9. The method of claim 1 wherein said compound or mixture is combined with an antiaggregation pheromone selected from the group consisting of verbenone and 3-methylcyclohex-2-ene-1-one.

10. The method of claim 2 wherein said compound or mixture is combined with an antiaggregation pheromone selected from the group consisting of verbenone and 3-methylcyclohex-2-ene-1-one.

11. The method of claim 3 wherein said compound or mixture is combined with a green leaf volatile, or mixtures thereof, and an antiaggregation pheromone selected from the group consisting of verbenone and 3-methylcyclohex-2-ene-1-one.

12. The method of claim 4 wherein said compound or mixture is combined with a green leaf volatile, or mixtures thereof, and an antiaggregation pheromone selected from the group consisting of verbenone and 3-methylcyclohex-2-ene-1-one.

13. The method of claim 1 wherein said conifer-infesting bark beetles are selected from the group consisting of *Dendroctonus ponderosae, Dendroctonus rufipennis, Dendroctonus pseudotsugae, Ips pini,* and *Dryocoetes confusus.*

14. The method of claim 2 wherein said conifer-infesting bark beetles are selected from the group consisting of *Dendroctonus ponderosae, Dendroctonus rufipennis, Dendroctonus pseudotsugae, Ips pini,* and *Dryocoetes confusus.*

15. The method of claim 3 wherein said conifer-infesting bark beetles are selected from the group consisting of *Dendroctonus ponderosae, Dendroctonus rufipennis, Dendroctonus pseudotsugae, Ips pini,* and *Dryocoetes confusus.*

16. The method of claim 4 wherein said conifer-infesting bark beetles are selected from the group consisting of *Dendroctonus ponderosae, Dendroctonus rufipennis, Dendroctonus pseudotsugae, Ips pini,* and *Dryocoetes confusus.*

17. A composition for repelling conifer-infesting bark beetles consisting essentially of an effective amount of a repellent compound selected from the group consisting of: toluene, pentanol, 2-hexanone, 3-hexanone, heptanal, 2-hydroxycyclohexanone, (E)-ocimene, conophthorin, guiacol, nonanal, methylsalicylate, decanal, thymolmethylether, (E)-nerolidol and dendrolasin, or mixtures thereof, and an acceptable carrier.

18. The composition for repelling conifer-infesting bark beetles consisting essentially of an effective amount of a repellent compound selected from the group consisting of: heptanal, conophthorin, guiacol, nonanal, methylsalicylate, decanal and (E)-nerolidol, or mixtures thereof and an acceptable carrier.

19. The composition of claim 17, wherein said repellent compound or mixture is combined with a green leaf volatile selected from the group consisting of hexanal, (E)-2-hexenal, 1-hexanol, (E)-2-hexen-1-ol, (Z)-2-hexen-1-ol, and (Z)-3-hexen-1-ol, and mixtures thereof.

20. The composition of claim 18, wherein said repellent compound or mixture is combined with a green leaf volatile selected from the group consisting of hexanal, (E)-2-hexenal, 1-hexanol, (E)-2-hexen-1-ol, (Z)-2-hexen-1-ol, and (Z)-3-hexen-1-ol, and mixtures thereof.

21. The composition of claim 17, wherein said repellent compound or mixture is combined with an antiaggregation pheromone selected from the group consisting of verbenone and 3-methylcyclohex-2-ene-1-one.

22. The composition of claim 18, wherein said repellent compound or mixture is combined with an antiaggregation pheromone selected from the group consisting of verbenone and 3-methylcyclohex-2-ene-1-one.

23. The composition of claim 17, wherein said repellent compound or mixture is combined with a green leaf volatile, or mixtures thereof, and an antiaggregation pheromone selected from the group consisting of verbenone and 3-methylcyclohex-2-ene-1-one.

24. The composition of claim 18, wherein said repellent compound or mixture is combined with a green leaf volatile, or mixtures thereof, and an antiaggregation pheromone selected from the group consisting of verbenone and 3-methylcyclohex-2-ene-1-one.

\* \* \* \* \*